(12) United States Patent
Steinert et al.

(10) Patent No.: US 6,852,686 B2
(45) Date of Patent: Feb. 8, 2005

(54) METHODS FOR AMELIORATING ICTHYOSIFORM SKIN DISEASES

(75) Inventors: Peter Steinert, Bethesda, MD (US); Lyuben Marekov, Rockville, MD (US); Zoltan Nemes, Debrecen (HU)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 101 days.

(21) Appl. No.: 10/023,275

(22) Filed: Dec. 13, 2001

(65) Prior Publication Data

US 2003/0072795 A1 Apr. 17, 2003

Related U.S. Application Data

(63) Continuation of application No. PCT/US00/17235, filed on Jun. 22, 2000.
(60) Provisional application No. 60/140,656, filed on Jun. 23, 1999.

(51) Int. Cl.[7] ...................... A61K 38/00; A61K 31/155; A61K 31/08; A61K 31/04; A61K 38/53
(52) U.S. Cl. .......................... 514/2; 514/613; 514/724; 514/740; 424/94.5; 424/450; 435/193; 530/353
(58) Field of Search ................................ 424/94.5, 450; 514/2, 613, 724, 740; 435/193; 530/353

(56) References Cited

U.S. PATENT DOCUMENTS

| | | | | |
|---|---|---|---|---|
| 5,525,336 A | * | 6/1996 | Green et al. | 424/94.5 |
| 6,165,500 A | * | 12/2000 | Cevc | 424/450 |
| 6,274,364 B1 | * | 8/2001 | Bernard et al. | 435/212 |

FOREIGN PATENT DOCUMENTS

| | | |
|---|---|---|
| WO | 9322281 | 11/1993 |
| WO | 9418945 | 9/1994 |

OTHER PUBLICATIONS

Lai et al., "Sphingosylphosphocholine Reduces the Calcium Ion Requirement for Activating Tissue Transglutaminase" (Jun. 27, 1997) Journal of Biological Chemistry, 272(26), 16295–16300.□□□□.*
Candi, E., et al. (1998) Transglutaminase 1 Mutations in Lamellar Ichthyosis. J. Biol. Chem. 273(22): 13693–13702.
Marekov, L. N. and Steinert, P. M. (1998) Ceramides Are Bound to Structural Proteins of the Human Foreskin Epidermal Confirmed Cell Envelope. J. Biol. Chem. 273(28): 17763–17770.
Nemes, Z. and Steinert, P. M. (1999) Bricks and mortar of the epidermal barrier. Exp. Mol. Med. 31(1):5–19.
Nemes, Z., et al. (1999) A novel function for transglutaminase 1: Attachment of long–chain ω–hydroxyceramides to involucrin by ester bond formation. PNAS 96:8402–8407.
Nemes, Z., et al. (1999) Involucrin Cross–linking by transglutaminase 1 Binding to Membranes Directs Residue Specificity. J. Biol Chem. 274(16):11013–11021.
Steinert, P. (Presentation Apr. 19, 1999) Enzymatic Attachment of Ceramides to the Cornified Cell Envelope. Gordon Research Conference on the Barrier Function of Mammalian Skin, Il Ciocco, Barga, Italy (Apr. 18–23, 1999).
Steinert, P. M., et al. (1998) Biochemical Evidence That Small Proline–rich Proteins and Trichohyalin Function in Epithelia by Modulation of the Biomechanical Properties of Their Cornified Cell Envelopes. J. Biol. Chem. 273(19):11758–11769.

* cited by examiner

*Primary Examiner*—Michael Meller
*Assistant Examiner*—Jennifer Ione Harle
(74) *Attorney, Agent, or Firm*—Knobbe, Martens, Olson & Bear, LLP

(57) ABSTRACT

The present invention relates to the discovery of a method to provide stabilized transglutaminase 1 enzyme, involucrin, and other molecules necessary for the assembly of the cell envelope to skin cells. Novel biological tools, prophylactics, therapeutics, cosmetics, and methods of use of the foregoing for study, prevention, and treatment of skin disorders are also disclosed.

4 Claims, 20 Drawing Sheets

METHODS FOR AMELIORATING ICTHYOSIFORM SKIN DISEASES

CROSS-REFERENCE TO RELATED APPLICATIONS

This application is a continuation of international application number PCT/US00/17235, and claims the benefit of priority of international application number PCT/US00/17235 having international filing date of Jun. 22, 2000, designating the United States of America and published in English, which claims the benefit of priority of U.S. provisional patent application No. 60/140,656, filed Jun. 23, 1999; both of which are hereby expressly incorporated by reference in their entireties.

FIELD OF THE INVENTION

The present invention relates to the discovery of a method to provide stabilized transglutaminase 1 enzyme, involucrin, and other molecules to skin cells. Novel biological tools, prophylactics, therapeutics, cosmetics, and methods of use of the foregoing for study, prevention, and treatment of skin disorders are also disclosed.

BACKGROUND OF THE INVENTION

Terrestrial vertebrates protect themselves from chemical and physical damage and uncontrolled water loss by maintaining a barrier in their epidermis. In mammals this is accomplished by forming a highly insoluble protein and lipid structure on the surface of the corneocytes termed the cornified envelope (CE) and by impeding water diffusion across the stratum corneum by mortaring together the corneocytes by layers of hydrophobic skin specific lipids. (Downing et al., *Dermatology in General Medicine*, Fitzpatrick, et al., eds., pp. 210–221 (1993) and Ponec, M., *The Keratinocyte Handbook*, Leigh, et al., eds., pp. 351–363 (1994)). These lipids differ in composition from other bilayer forming lipids found in all living cells. Notably they have a diminished phospholipid content and, instead, contain increased amounts of cholesterol, its acyl and sulfate esters, fatty acids, and several epidermal specific long chain hydroxy- and hydroxyacyl (glucosyl)-ceramides. (Elias, P. M. and G. K. Menon, *Skin Lipids, Advances in Lipid Research*, Vol. 24, pp. 1–26 (1991)).

Synthesis of the lipids that join the CE is initiated in the spinous layer. These lipids are temporarily stored in lamellar bodies of stratum granulosum, where they are arranged as stacks of tetralaminar sheets. Preceding or paralleling the formation of the protein barrier of the CE, the contents of the lamellar bodies are extruded into the intercellular space. One component of these lipids are epidermal specific long chain ω-hydroxyceramides, which become covalently attached onto the outer surface of the CE as a ~5 nm monomolecular layer. One idea is that these protein-linked ceramides interdigitate with the intercellular lipid in a comb-like fashion, presumably to stack them into ordered lamellae. (Wertz, P. W., *Experientia Suppl.*, 78: 227–237 (1997) and Wertz, P. W. and D. T. Downing, *Physiology, Biochemistry and Molecular Biology of the Skin*, Goldsmith, L. A., ed., Vol. 1, pp. 205–236 (1991)).

Many icthyosiform diseases (e.g., autosomal recessive lamellar ichthyosis and recessive congenital nonbullous ichthyosiform erythroderma) are caused by improper or incomplete lipid barrier function. For example, Lamellar Ichthyosis (LI) is a clinically heterogeneous autosomal recessive disorder, which causes abnormalities of the CE and persons with the severe LI phenotype often present at birth encased in a translucent colloidion membrane. Soon after birth, this thick membrane dries and cracks and, over time, these persons develop large, brown, plate-like scales in a generalized distribution. (Russell et al., *Nat. Genet.* 9:279 (1995)).

The locus for LI has been mapped to chromosome 14q11 and a complete linkage with the gene encoding transglutaminase 1 (TGase 1) was found. (Russell et al., *Nat. Genet.* 9:279 (1995)). Further, point mutations in TGase 1 were identified in two of the multiplex LI families used in the linkage study. (Russell et al., *Nat. Genet.* 9:279 (1995)). These mutations are hypothesized to adversely affect the formation of cross-links essential in the production of the CE. (Russell et al., *Nat. Genet.* 9:279 (1995)).

To form a healthy CE, specialized keratinocyte proteins are expressed and subsequently made insoluble by cross-linking by both disulfide bonds and isopeptide bonds formed by transglutaminases (TGases). (Matoltsy, A. G. and M. N. Matoltsy, *J. Invest Dermatol.*, 46: 127–129 (1966); Sun, T-T. and H. Green, *Cell*, 9: 511–521 (1976); Greenberg, et al., *FASEB J.*, 5: 3071–3077 (1991); Reichert, et al., *Molecular Biology of the Skin*, Darmon, M. and M. Blumenberg eds., pp. 107–150 (1993); and Simon, M., *The Keratinocyte Handbook*, Leigh, et al., eds., pp. 275–292 (1994)). Several investigators believe that the protein composition of CEs varies widely between epithelia and even different body sites of epithelia such as the epidermis. (Steinert, et al. *J. Biol. Chem.*, 273: 11758–11769 (1998) and Song, et al., *Genomics*, 55:28–42 (1999)). However, involucrin seems to be a ubiquitous component of most if not all CEs. (Simon, M., *The Keratinocyte Handbook*, Leigh, et al., eds., pp. 275–292 (1994) and Steinert, P. M. and L. N. Marekov, *J. Biol. Chem.*, 272: 2021–2030 (1997)).

The function of involucrin can be characterized as that of a protein scaffold since it is one of the first proteins deposited at or near the membrane surface in the vicinity of desmosomes to initiate CE formation and is subsequently joined to several reinforcement proteins, as well as, ceramide lipids. (Steinert, P. M. and L. N. Marekov, *J. Biol. Chem.*, 272: 2021–2030 (1997); Rice, R. H. and H. Green, *Cell*, 18: 681–694 (1979); Simon, M. and H. Green, *Cell*, 36: 827–834 (1984); Yaffe et al., *J. Invest. Dermatol.*, 100: 3–9 (1993); Crish et al., *Differentiation*, 53: 191–200 (1993); Steinert, P. M., *Cell Death Different.*, 2: 33–40 (1995); Ishida-Yamamoto, et al., *J. Invest. Dermatol.*, 108: 12–16 (1997); Candi et al., *Proc. Natl. Acad. Sci. USA*, 95: 2067–2072 (1998)); and (Marekov, L. N. and P. M. Steinert, *J. Biol. Chem.*, 273: 17763–17770 (1998)). Expression studies, for example, demonstrate that involucrin deposition at the cell periphery precedes all other suspected or confirmed CE protein constituents. (Rice, R. H. and H. Green, *Cell*, 11: 417–422 (1979); Watt, F. M. and H. Green, *J. Cell Biol.*, 90: 738–742 (1981); Simon, M. and H. Green, *Cell*, 36: 827–834 (1984); Simon, H. and H. Green, *J. Biol. Chem.*, 263: 18093–18098 (1988); Yaffe, et al., *J. Biol. Chem.*, 267: 12233–12238 (1992); Yaffe, et al., *J. Invest. Dermatol.*, 100: 3–9 (1993); Crish, et al., *Differentiation*, 53: 191–200 (1994); and de Viragh, et al., *J. Invest. Dermatol.*, 103: 815–819 (1994)).

Additionally, shadowing and scanning transmission electron microscopy have revealed that a monomolecular layer of involucrin is overlayered on the cytoplasmic side by other CE structural proteins. (Jarnik, et al., *J. Cell Sci.*, 111: 1051–1060 (1998)). Further, extant models of CE structure based on biochemical characterization and protein sequencing indicate that involucrin becomes cross-linked to several reinforcement CE proteins including other molecules of involucrin, trichohyalin, elafin, repetin, periplakin, desmoplakin, envoplakin, keratin intermediate filaments, members of the small proline rich family, cystatin α, and loricrin. (Steinert, et al. *J. Biol. Chem.*, 273: 11758–11769 (1998); Steinert, P. M. and L. N. Marekov, *J. Biol. Chem.*, 272: 2021–2030 (1997); and Robinson, et al.,*J. Biol. Chem.*, 272: 12035–12036 (1997)). Still further, recent data have shown that involucrin is a major target for the covalent attachment of ceramide lipids from the exterior surface of the CE, which could only occur if involucrin was deposited in the intimate vicinity of the keratinocyte membrane at an early time. (Marekov, L. N. and P. M. Steinert, *J. Biol. Chem.*, 273: 17763–17770 (1998)).

Human involucrin contains 150 glutamine and 45 lysine residues and it appears that mammalian involucrins have undergone extensive expansion of various glutamine-rich repeating motifs during evolution perhaps to increase the sites suitable or available for TGase mediated cross-linking. (Eckert, R. L. and H. Green, *Cell*, 46: 583–589 (1988) and (Tseng, H. and H. Green, *Cell*, 54: 491–496 (1988)). Indeed, involucrin is an excellent substrate for transglutaminases (TGases) both in vitro and in vivo. (Simon, M. and H. Green, *J. Biol. Chem.*, 263: 18093–18098 (1998); Etoh et al., *Biochem. Biophys. Res. Commun.*, 136: 51–56 (1986); and (Steinert, P. M. and L. N. Marekov, *J. Biol. Chem.*, 272: 2021–2030 (1997)). Sequencing studies have shown, however, that only a limited number of these residues are used for cross-linking in vivo. (Steinert, P. M. and L. N. Marekov, *J. Biol. Chem.*, 272: 2021–2030 (1997)).

The human TGase 1 gene (TGase 1) encodes a 92-kDa protein consisting of 816 amino acid residues located on chromosome 14q11.2. (Kim et al., *J. Bio. Chem.* 267:7710–7717 (1992)). TGases are Ca2+-dependent enzymes, which catalyze the transfer of the γ-carboxyl group from protein-bound glutamine to the ε-amino group of protein bound lysine residues or other primary amines. These enzymes are responsible for the cross-linking of CE proteins into a chemically and mechanically resistant protein polymer. (Greenberg et al., *FASEB J.*, 5: 3071–3077 (1991); Reichert et al., *Molecular Biology of the Skin The Keratinocyte*, Darmon et al., eds., pp. 107–150 (1993); and Melino et al., *Meth. Enzymol.*, in press (1999)). Of the seven known human TGases, four (TGases 1, 2, 3 and X) are expressed in terminally differentiating epithelia such as the epidermis. (Aeschlimann et al., *J. Biol. Chem.*, 273: 3452–3460 (1998) and Kim et al., *J. Biol. Chem.*, 266: 536–539 (1991)). Of these, the TGase 2 enzyme is thought to play only a minor role, and the properties of the newly discovered TGase X enzyme await characterization.

The TGase 1 and 3 enzymes are essential for the cooperative cross-linking of such substrates as loricrin, trichohyalin, and small proline rich proteins 1 and 2. (Candi, et al., *J. Biol. Chem.*, 274:7226–7237 (1999); (Tarcsa, et al., *J. Biol. Chem.*, 272: 27893–27901 (1997); (Candi, et al., *J. Biol. Chem.*, 270: 26382–26390 (1995); and (Tarcsa, et al., *J. Biol. Chem.*, 273: 23297–23303 (1998)). The TGase 3 enzyme is soluble and requires proteolytic activation before it can function. (Kim, et al., *J. Biol. Chem.*, 265: 21971–21978 (1990)). The TGase 1 enzyme was first discovered in keratinocytes and is usually anchored to membranes by way of acyl N-myristoyl and S-myristoyl or S-palmitoyl adducts near the amino terminus of the protein. (Chakravarty, R. and R. H. Rice, *J. Biol. Chem.*, 264: 625–629 (1989); Phillips, et al., *Biochemistry*, 32: 11057–11063 (1993); and Steinert, et al., *J. Biol. Chem.*, 271: 26242–26250 (1996)). While involucrin appears to be a good substrate for TGases in in vitro reactions, extant data have provided no information on which of these enzyme(s) are responsible for cross-linking in vivo.

Clearly, several crucial pieces of the puzzle are missing and a better understanding of CE assembly and ceramide lipid attachment would enable the development of novel biotechnological tools, therapeutics, prophylactics and cosmetics for the study, treatment and prevention of icthyosiform diseases and other related skin disorders.

BRIEF SUMMARY OF THE INVENTION

The present invention relates to the discovery of a method to provide stabilized transglutaminase 1 enzyme, involucrin, and other molecules necessary for the assembly of the cell envelope to skin cells. Novel biological tools, prophylactics, therapeutics, cosmetics, and methods of use of the foregoing for study, prevention, and treatment of skin disorders are also disclosed.

(A) Sucrose-loaded synthetic lipid vesicles (SLV) containing a total of 2 μmol of lipid were formulated with 0–30 mole % dipalmitoyl phosphatidylserine (PS). Approximately 1.2 nmol of recombinant purified human involucrin was added to the SLV in the presence of 1 mM $Ca^{++}$ at 23° C. The binding was assessed by measurement of protein concentrations in the supernatants before and after pelleting the SLV by ultracentrifugation. The Hill coefficient of the fitted sigmoidal regression curve is 3.82. Points represent the means±s.d. of three independent measurements. (B) Anionic phospholipids other than PS do not increase involucrin binding to SLV containing 8% PS: binding of involucrin to SLV containing 8% PS plus 0–20% phosphatidic acid (closed circles), phosphatidylglycerol (open circles), or phosphatidylinositol (closed triangles). Points represent the means±s.d. of three independent measurements.

Figure 2:
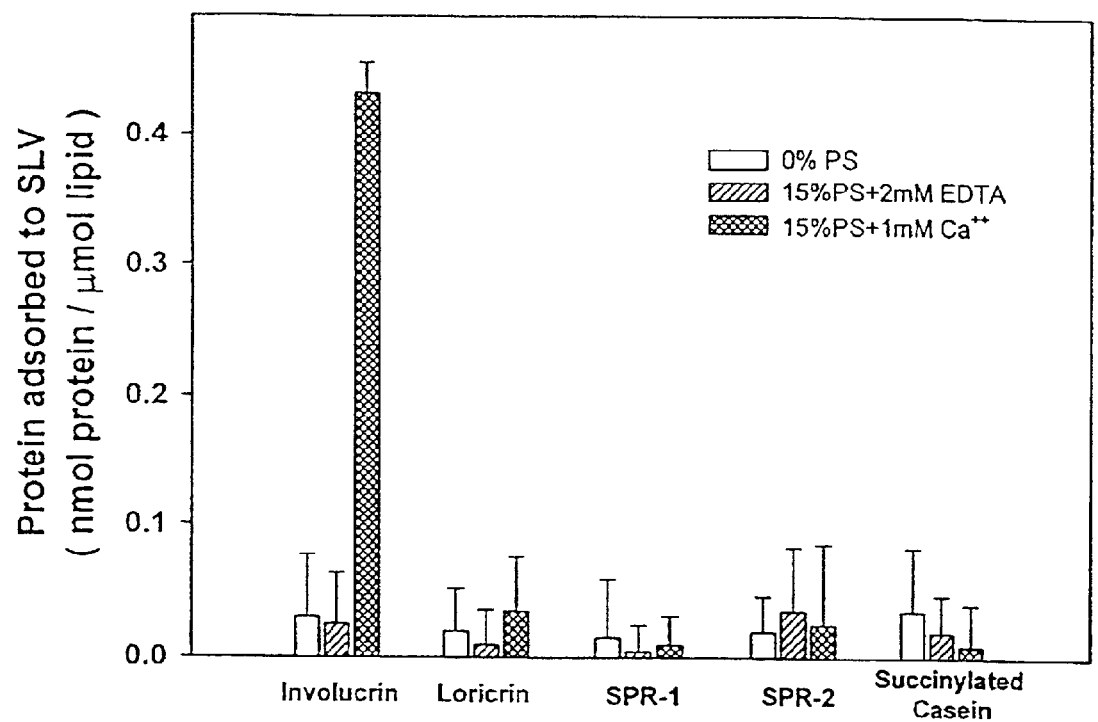

FIG. 2 Of Several in Vivo Substrates of the TGAasel Enzyme, Involucrin Binds to SLV.

Binding of excess amounts of recombinant human involucrin, loricrin, SPR1, SPR2 or succinylated casein to SLV formulated from 0 or 15% PS in the presence or absence of free $Ca^{++}$ was performed as in FIG. 1. Error bars represent the means±s.d. of three independent measurements. Values except for those of involucrin with 15% PS and 1 mM EDTA do not represent significant binding ($p>0.1$).

Figure 3:
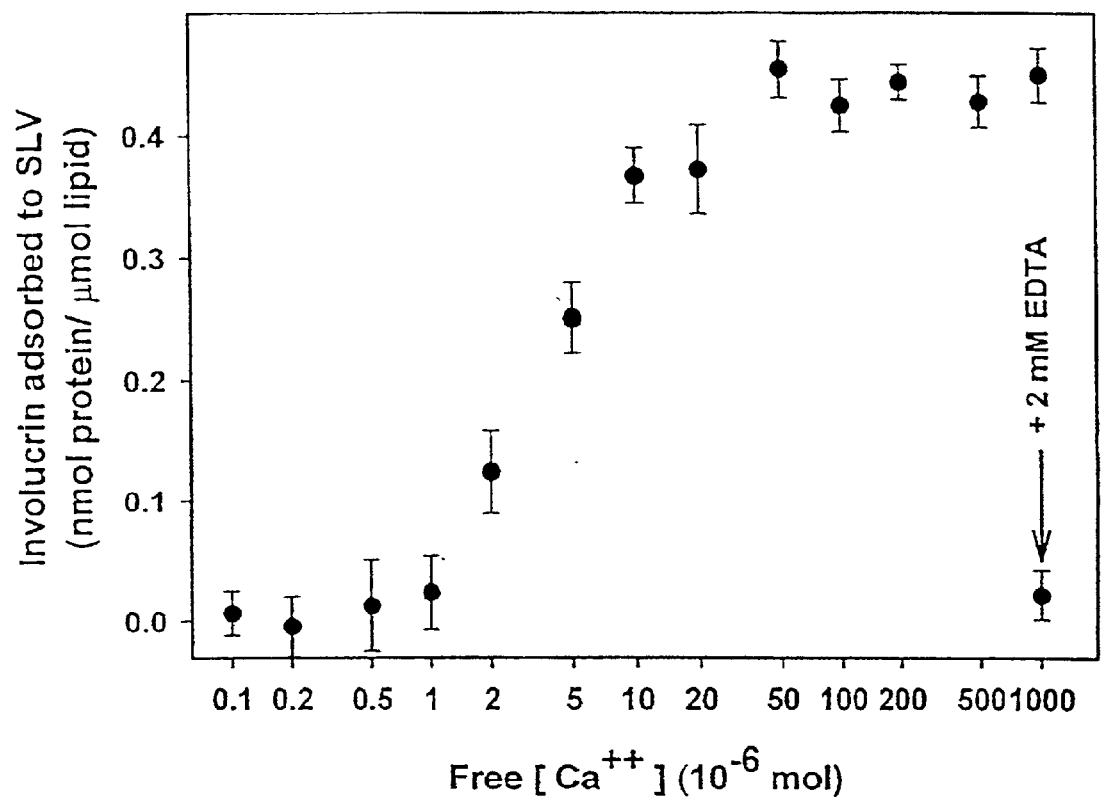

FIG. 3 Effect of Free $Ca^{++}$ Concentration on Involucrin Binding to SLV.

Involucrin binding was assayed as in FIG. 1 in the presence of 0–1000 μM $CaCl_2$. Half-maximal binding was calculated at 4.2±0.7 μM. Binding was reversible in the presence of EDTA. Points represent the means±s.d. of three independent measurements.

Figure 4:
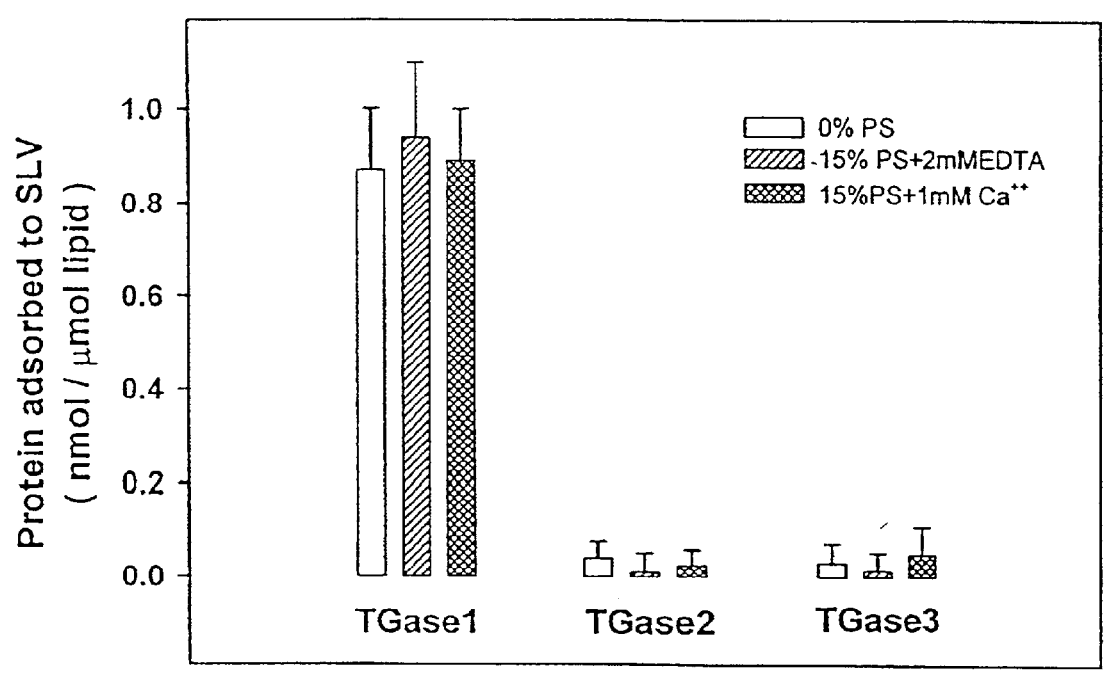

FIG. 4 Purified Recombinant TGase 1 Expressed in Baculovirus Spontaneously Associates to SLV.

Binding was assayed as in FIG. 1 in SLV formulated from 0 or 15% PS in the presence or absence of free $Ca^{++}$. Error bars represent the means±s.d. of three independent measurements. Binding of TGases 2 or 3 is not statistically significant ($p>0.1$).

Figure 5:
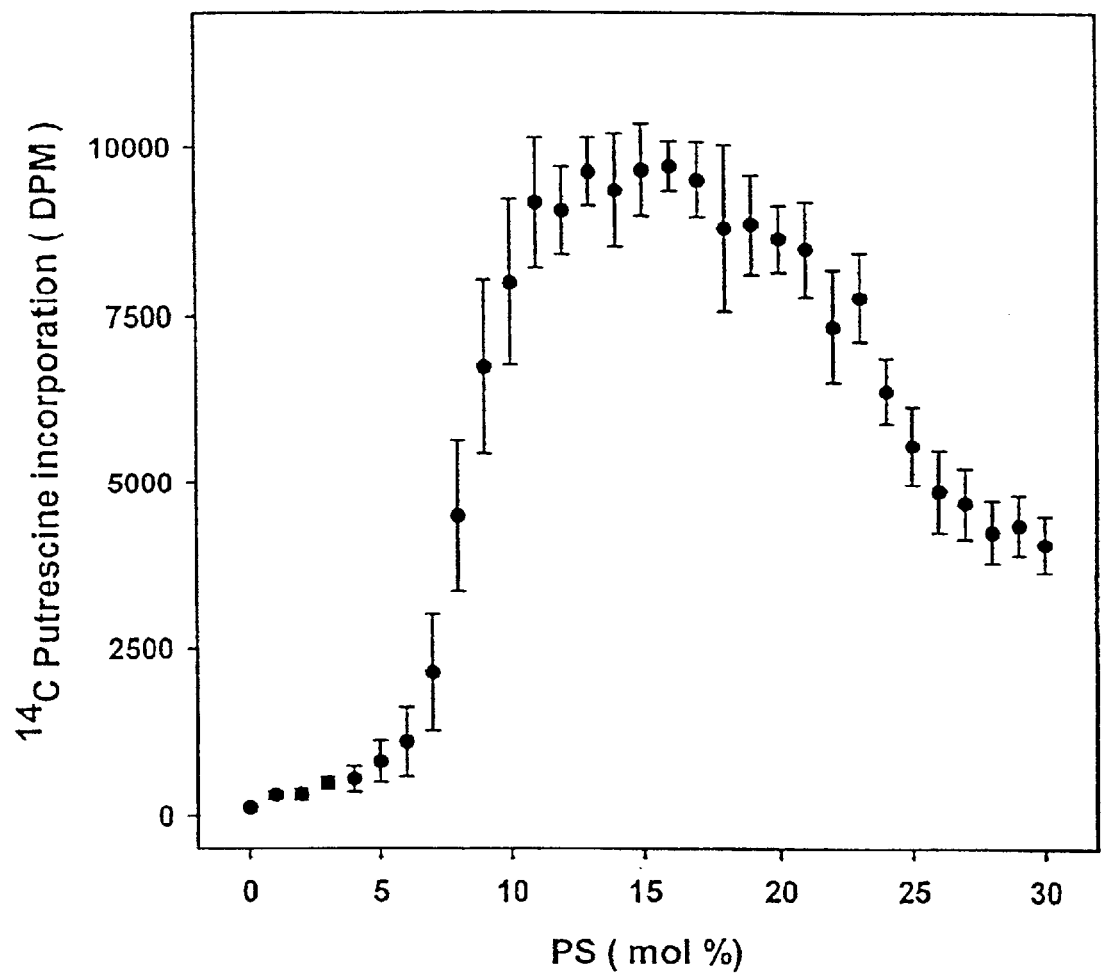

FIG. 5 Effect of PS Content of SLV on Incorporation of $^{14}C$-putrescine Into Involucrin by TGase 1.

TGase 1 (0.9 pmol) was bound to SLV formulated with 0–30% PS, to which were added 1.2 nmol of involucrin, 20 mM $^{14}$C-putrescine, and 1 mM Ca$^{++}$, and reacted for 30 min at 37° C. Incorporation of radioactivity shows a sigmoidal effect of PS between 3–12% and decline above 25% PS. Points represent the means±s.d. of three independent measurements.

Figure 6:
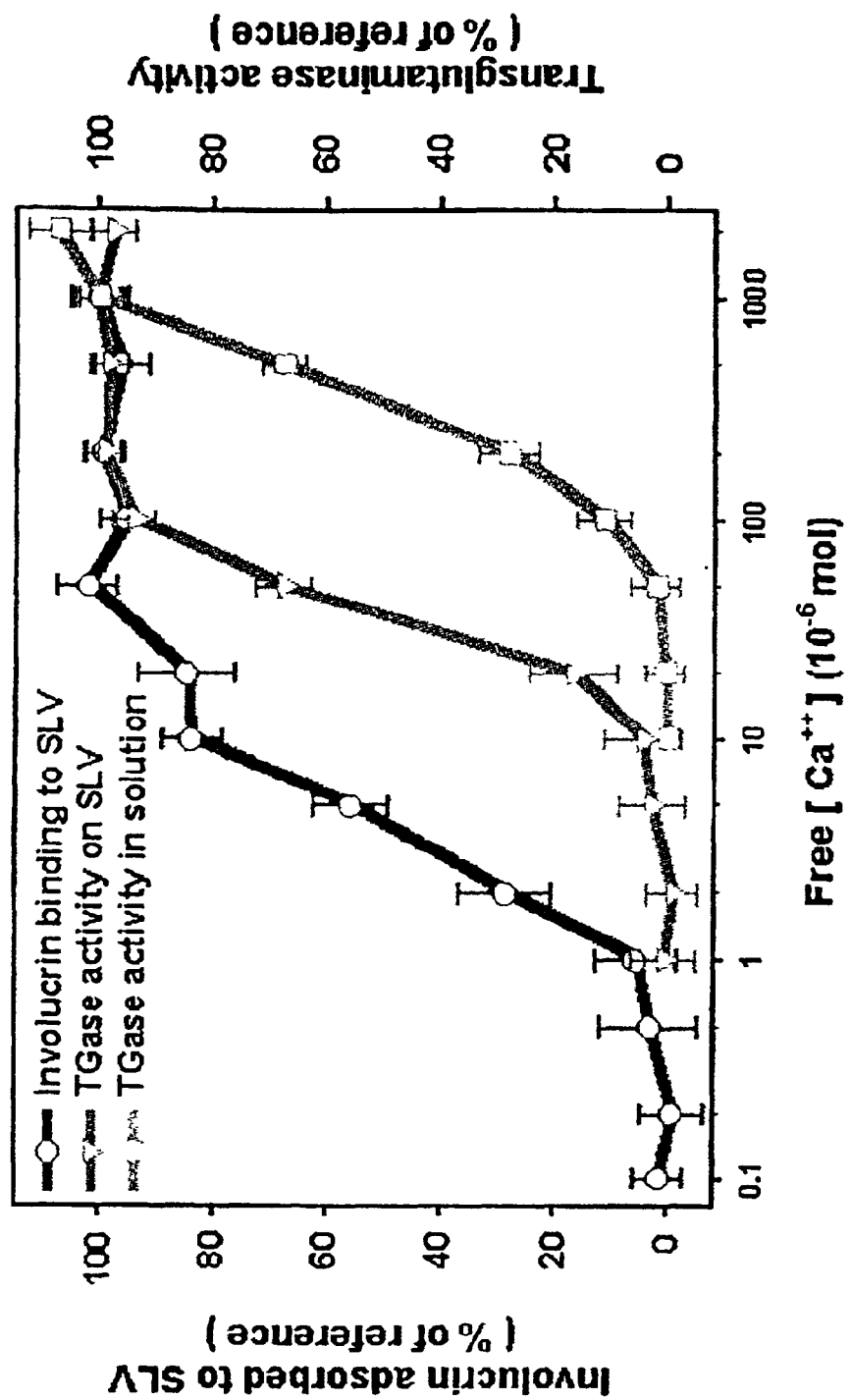

FIG. 6 Binding to SLV Lowers Free Ca$^{++}$ Ion Levels Required for Involucrin Cross-Linking by TGase 1.

$^{14}$C-Putrescine incorporation into 1.2 nmol of involucrin by TGase 1 was measured in the absence (squares) or presence (triangles) of SLV (2 μmol lipid) containing 15% PS at different free Ca$^{++}$ concentrations. Activity values are given as percent of the values measured at 1 mM Ca$^{++}$. Also shown for comparison are the data from FIG. 3; note that involucrin binds to SLV at much lower Ca$^{++}$ concentrations (circles). Points represent the means±s.d. of three independent measurements.

Figure 7:
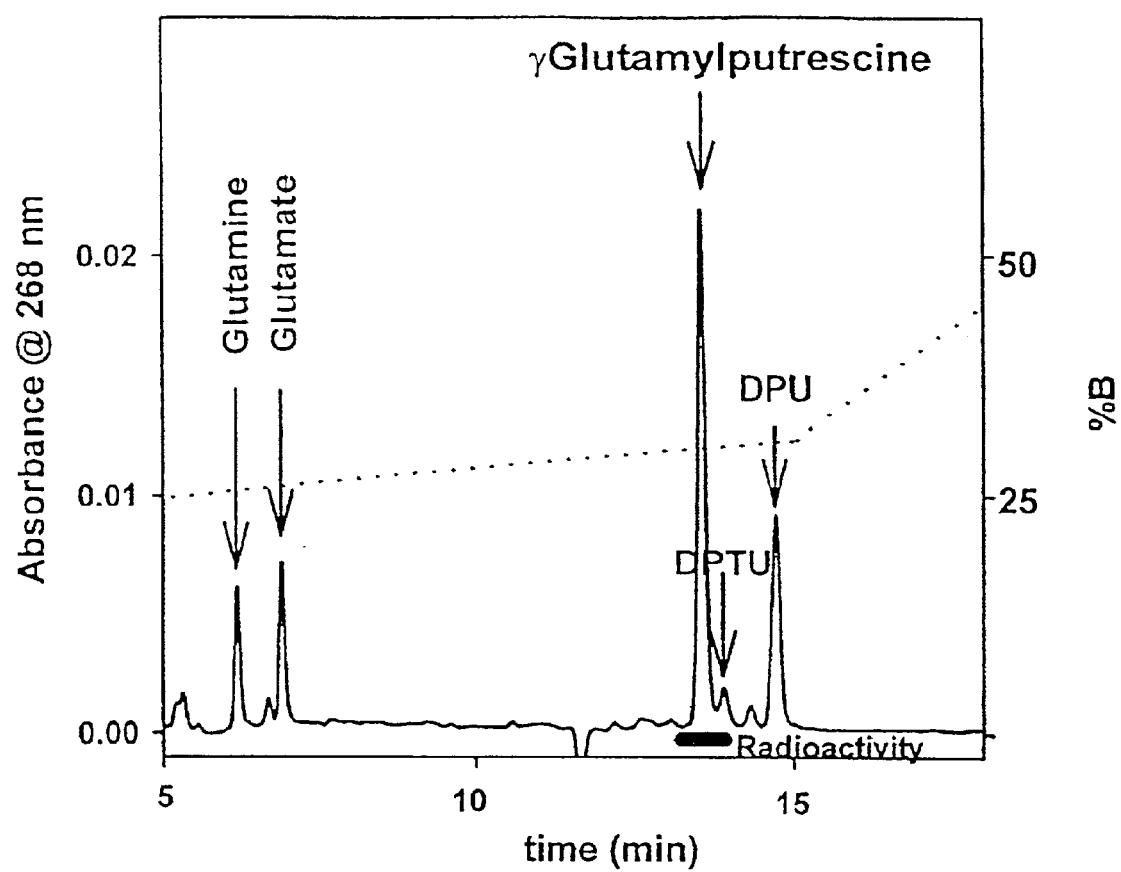

FIG. 7 Identification of (-Glutamylputrescine by Amino Acid Sequencing.

This assay identifies glutamine (Gln) residues that have been modified by putrescine as a result of the TGase reaction. After Edman degradation, the PTH-derivative of (-glutamylputrescine appears as a novel peak eluting at 13.55 min in the sequencing cycles where only a Gln residue would normally be expected. The relative amounts of this peak and that of PTH-Gln provide an estimate of the extent of modification.

Figure 8A:
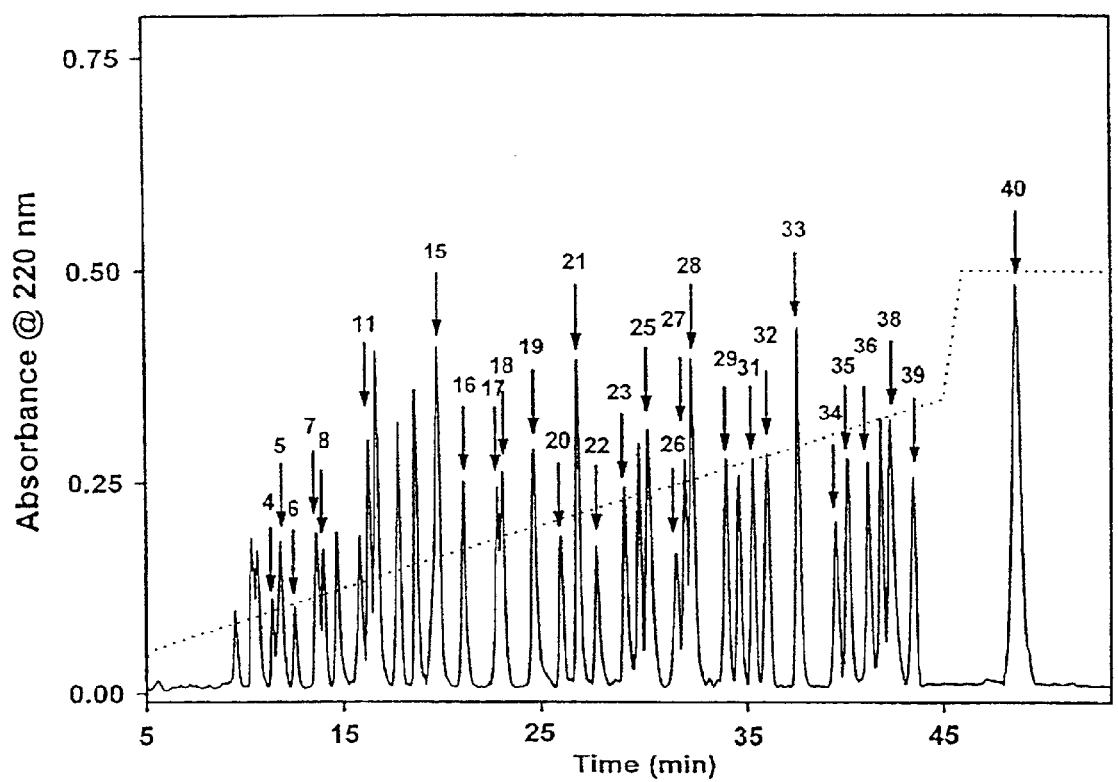
Figure 8B:
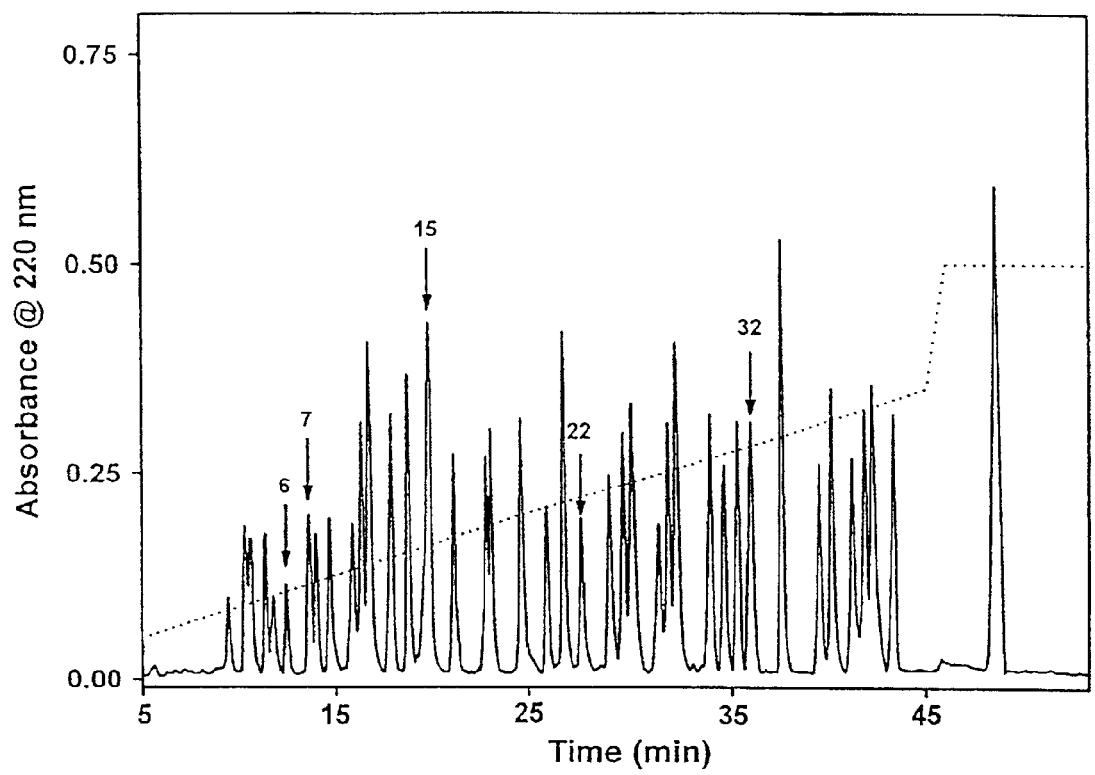

FIG. 8 Identification of Tryptic Peptides of Involucrin Labeled with $^{14}$C-Putrescine by Various Forms of TGase 1.

Involucrin was reacted with 20 mM $^{14}$C-putrescine using: (A), solubilized recombinant baculovirus TGase 1 not attached to SLV; and (B), TGase 1 bound to SLV containing 15% PS. Tryptic peptides of involucrin were separated by C18 reverse phase HPLC and were collected and assayed for isotope incorporation. Forty involucrin tryptic peptides were resolved in this system. Labeled peptides are shown by the numbered arrows. Note that in (B), additional minor peptide peaks were contributed by insect proteins, but the same numbering system was retained for clarity.

Figure 9:
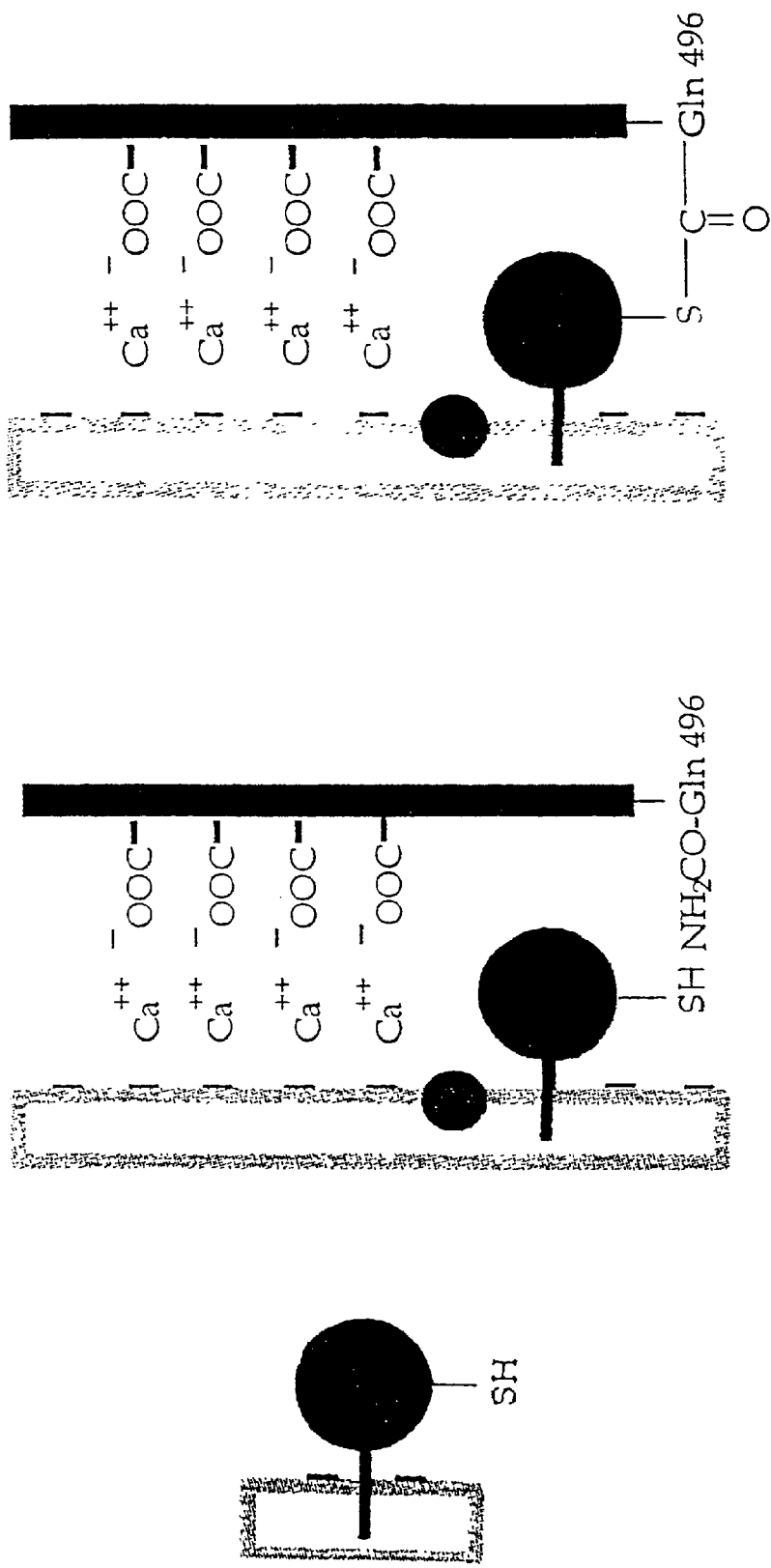

FIG. 9 Model for the Alignment of Involucrin and TGase 1 on SLV on the Inner Surface of the Plasma Membrane of Keratinocytes.

Newly expressed TGase 1 (large sphere) attaches to the membranes by way of the lipid adducts on its amino-terminal portion. As the Ca$^{++}$ concentration at the microenvironment of the membrane surface rises above a critical threshold level at the advent of terminal differentiation, and involucrin (thin rod) attaches spontaneously. This binding is fostered through ionic interactions of multiple Glu residues of involucrin, Ca$^{++}$, and the anionic PS-rich membrane surface (thick rod). We propose that these binding processes align only certain Gln residues of involucrin near the active site of juxtaposed TGase 1 molecules. Cross-linking reactions are initiated as the Ca$^{++}$ concentration rises further. The activated Gln residues can then be transferred to other nearby substrates including desmoplakin, envoplakin, etc. (small spheres) to initiate CE assembly.

FIG. 10 Comparison of a Natural ω-Hydroxyceramide and an Artifical ω-Hydroxyceramide.

(A) The structure of a natural ω-hydroxyceramide is shown. (B) The structure of the artificial substrate analog N-[16-(16-hydroxyhexadecyl)oxypalmitoyl]-sphingosine (lipid Z) is shown; note that the natural and the synthetic lipids have similar chain length and differ only by the presence of an (unreactive) ether bond.

Figure 11:
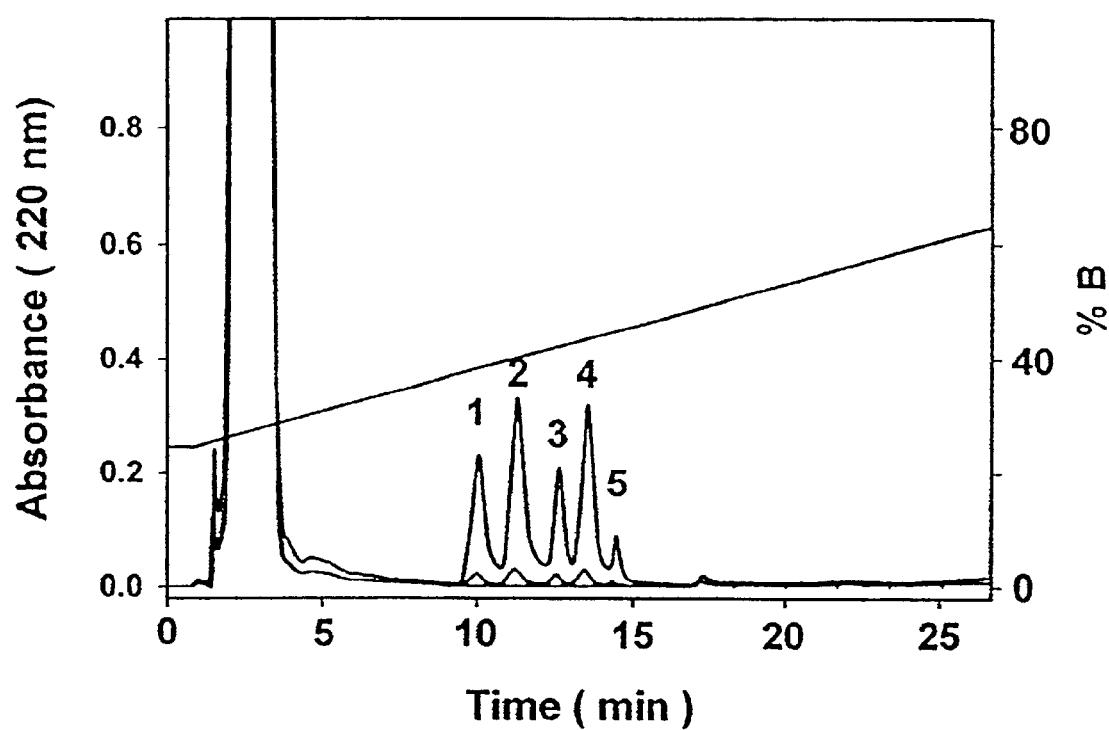

FIG. 11 Separation of Lipo-Peptide Adducts from the Tryptic Digest of Involucrin by HPLC.

Involucrin was reacted with SLV containing lipid Z in the presence of TGase 1. Lipid-attached hydrophobic peptides were selectively retained on a C4 column under strongly desorbing solvent conditions (sloping straight line). The numbered peaks refer to the corresponding lipo-peptides in FIG. 12 and Tables 3 and 4. In controls, no lipo-peptides were recovered in the presence of EDTA; and lipo-peptide amounts were significantly reduced by putrescine (see FIG. 14), or by 20 mM of the generic TGase inhibitor cystamine (smaller peaks shown with A$_{220}$ values of approximately 0).

Figure 12A:
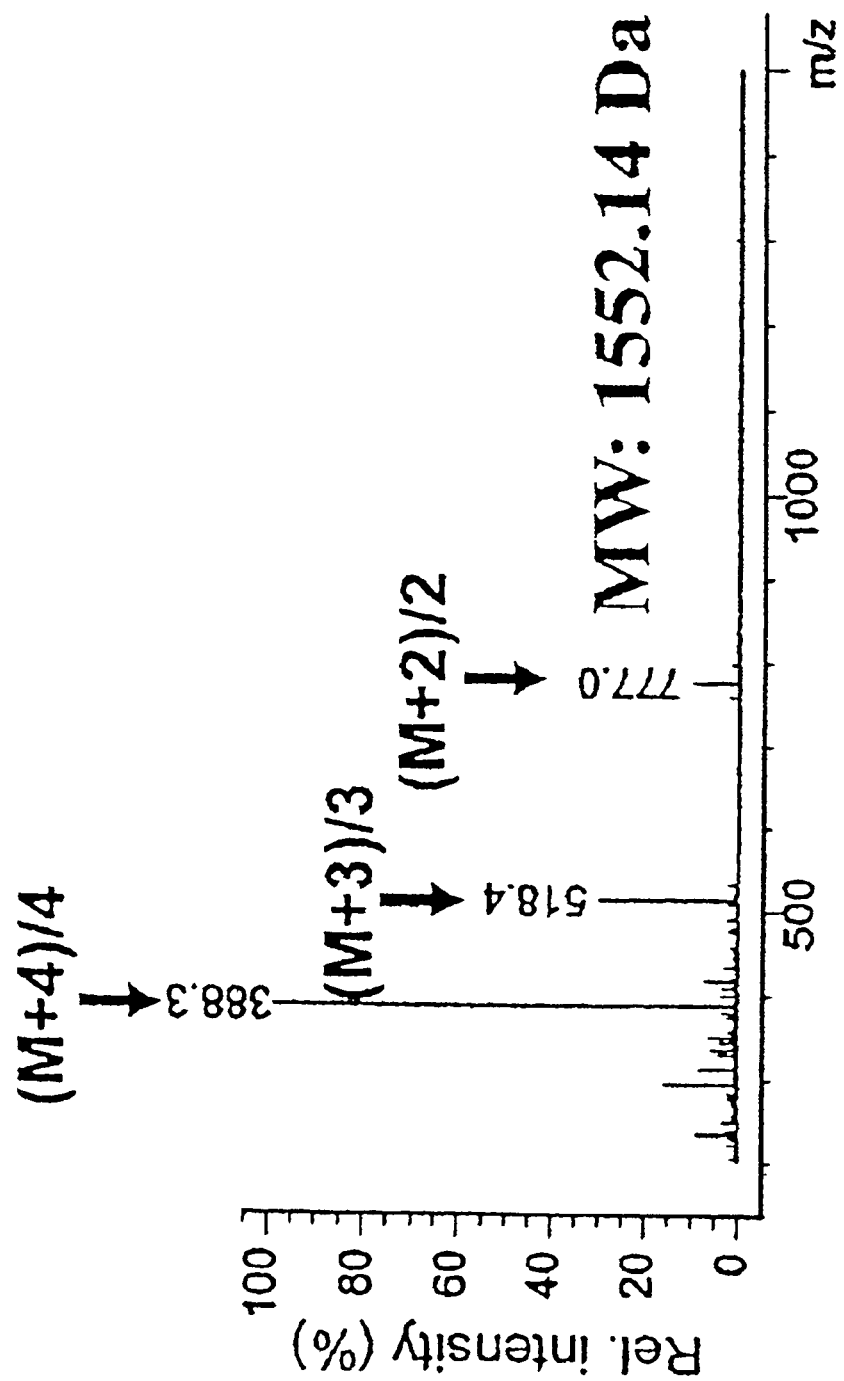
Figure 12B:
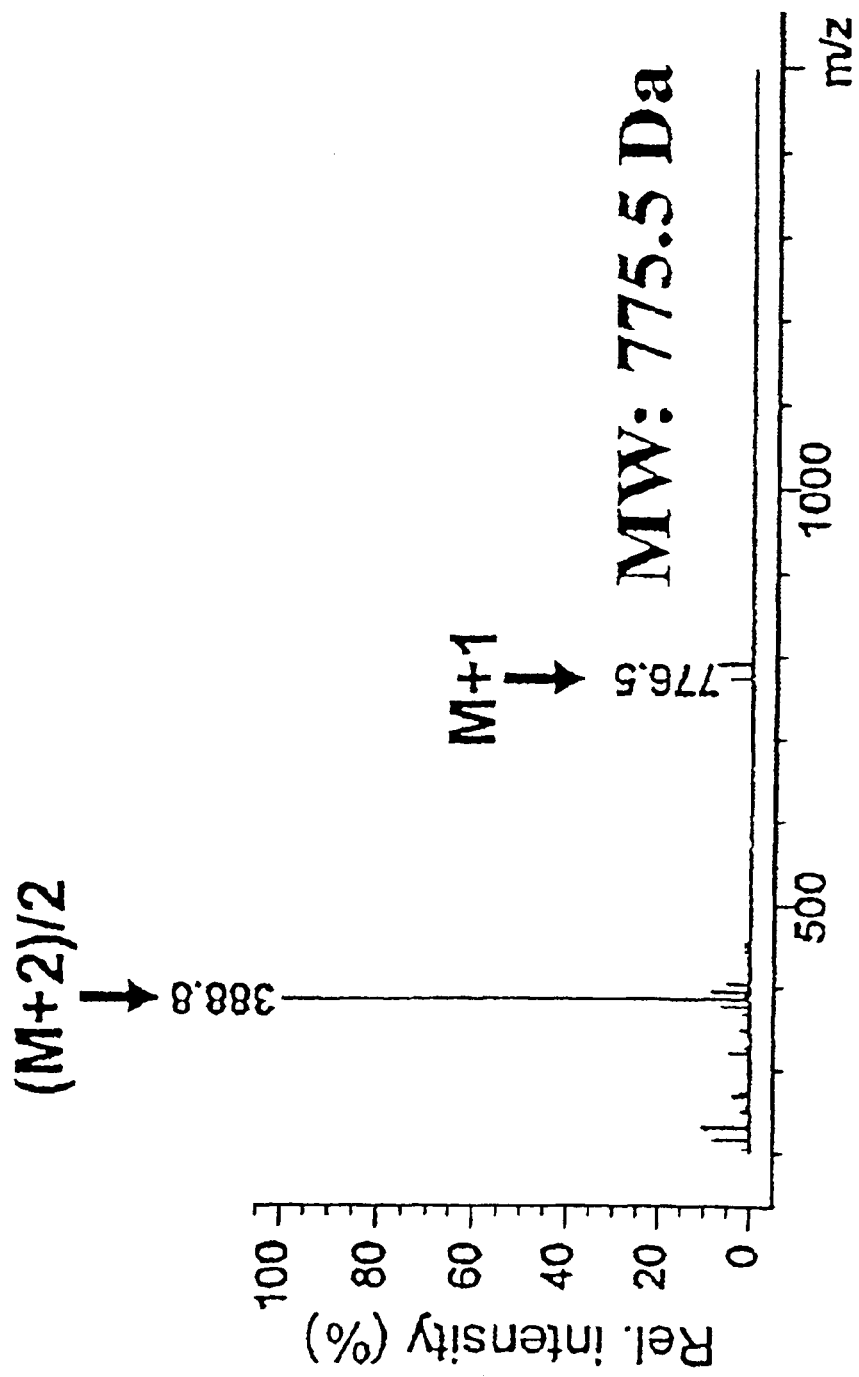

FIG. 12 Analysis of Peak 1 of FIG. 11 by Electrospray Ionization Mass Spectrometry Before (A) and After (B) Ssaponification.

Peaks with corresponding masses marked by arrows denote multiple charge states of the peptides used for mass determination. Charge states correspond to $m/z=(m+n)/n$ atomic mass units (n: number of charges). Saponification reduces the molar mass of peptides by 776 amu, indicating the loss by hydrolysis of one mol of lipid Z. (Lipid Z has a mass of 794.3 amu.). Deconvoluted masses for all five lipo-peptides are listed in Table 3.

Figure 13:
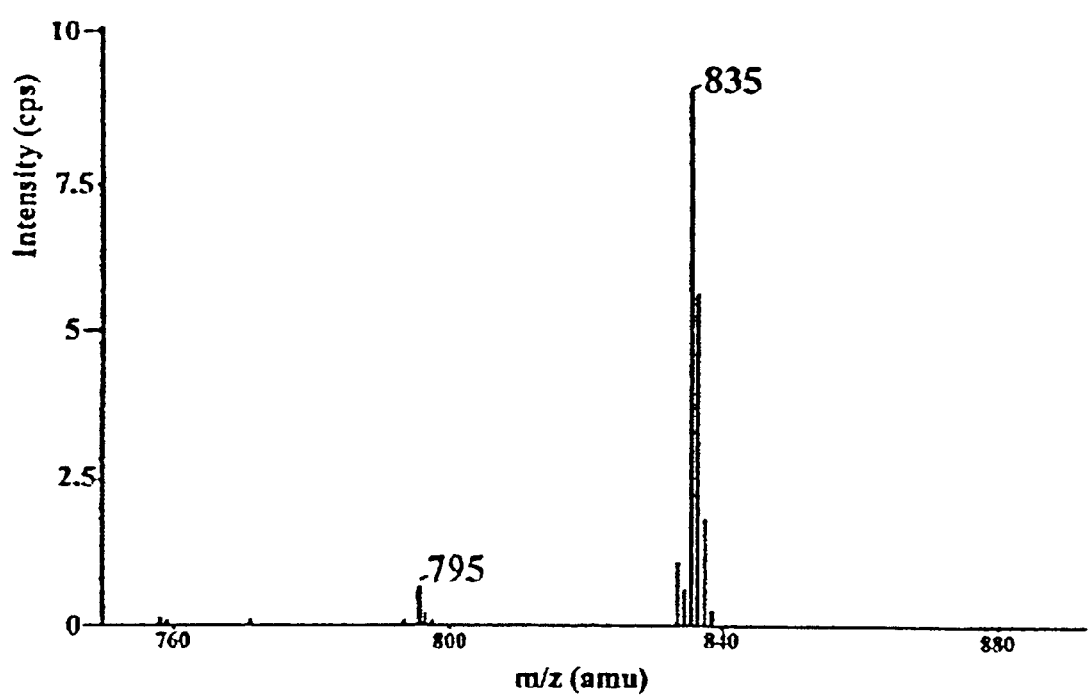

FIG. 13 Mass Sspectrometry of Lipid Z Following Acetonide Formation of its Peptide-Adducts and Subsequent Alkaline Hydrolysis.

Most of the Lipid Z (M+H+=795 amu) was recovered as its acetonide derivative (M+H+=835 amu), indicating that the hydroxyl groups of the sphingosine moiety in lipid Z are not involved in ester bond formation with involucrin.

FIG. 14 Inhibitory Effect of Putrescine on Glutaminyl Ester Formation by TGase 1.

Amounts of individual lipo-peptides were quantitated by amino acid analysis after isolation by C4 HPLC chromatography. Yields were related to the total of reactive Gln residues. (A) Ester modification of reactive glutamines without inhibitor. (B) 1 mM putrescine inhibited the formation of lipid adducts. (C) 20 mM putrescine significantly ($p<0.01$) reduced the amount of ester linkages when added to the reaction at 45 min, showing the availability of ester linkages for TGase mediated aminolysis. Values (means±s.e.m.) are from five separate experiments.

Figure 15A:
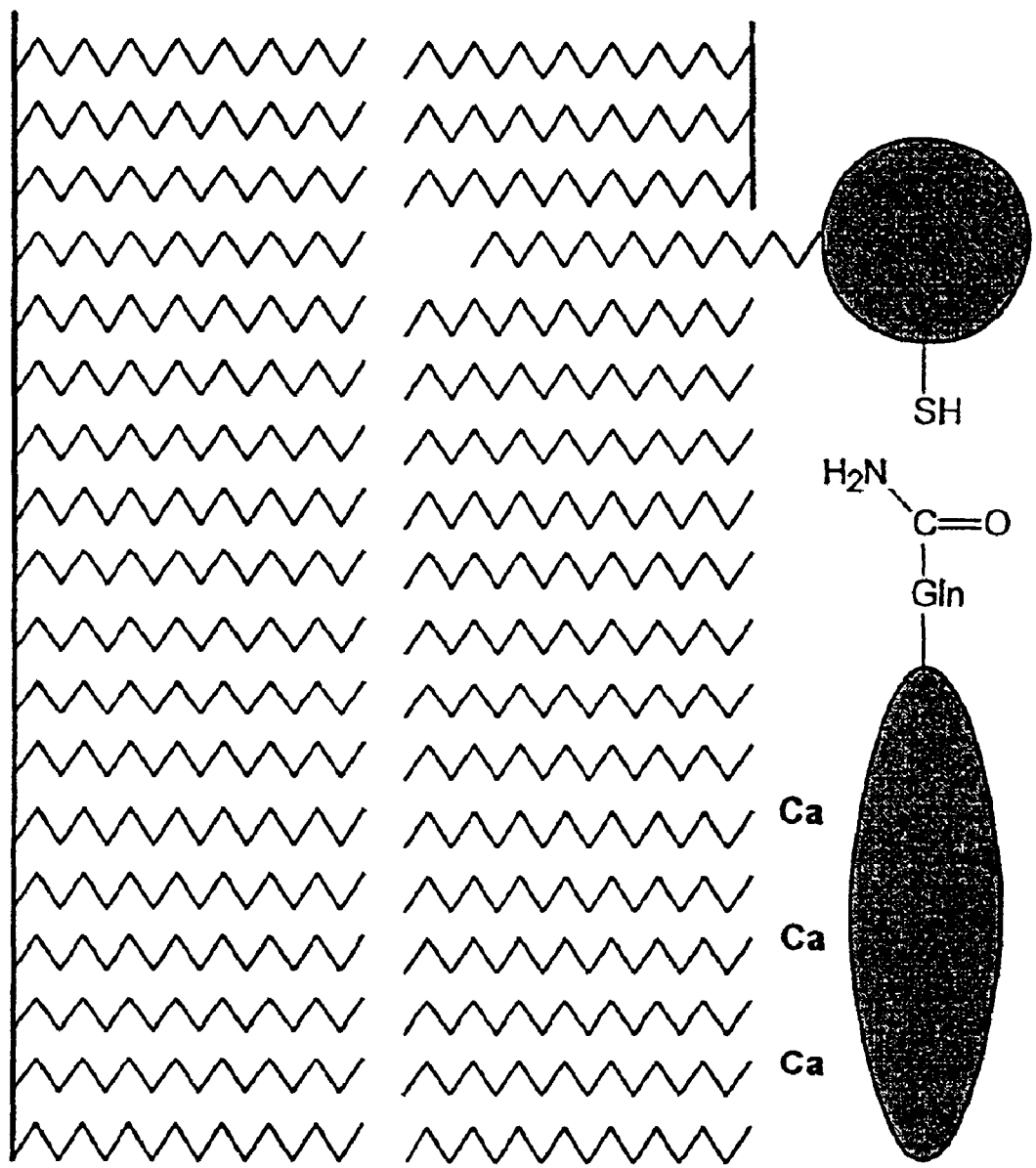
Figure 15B:
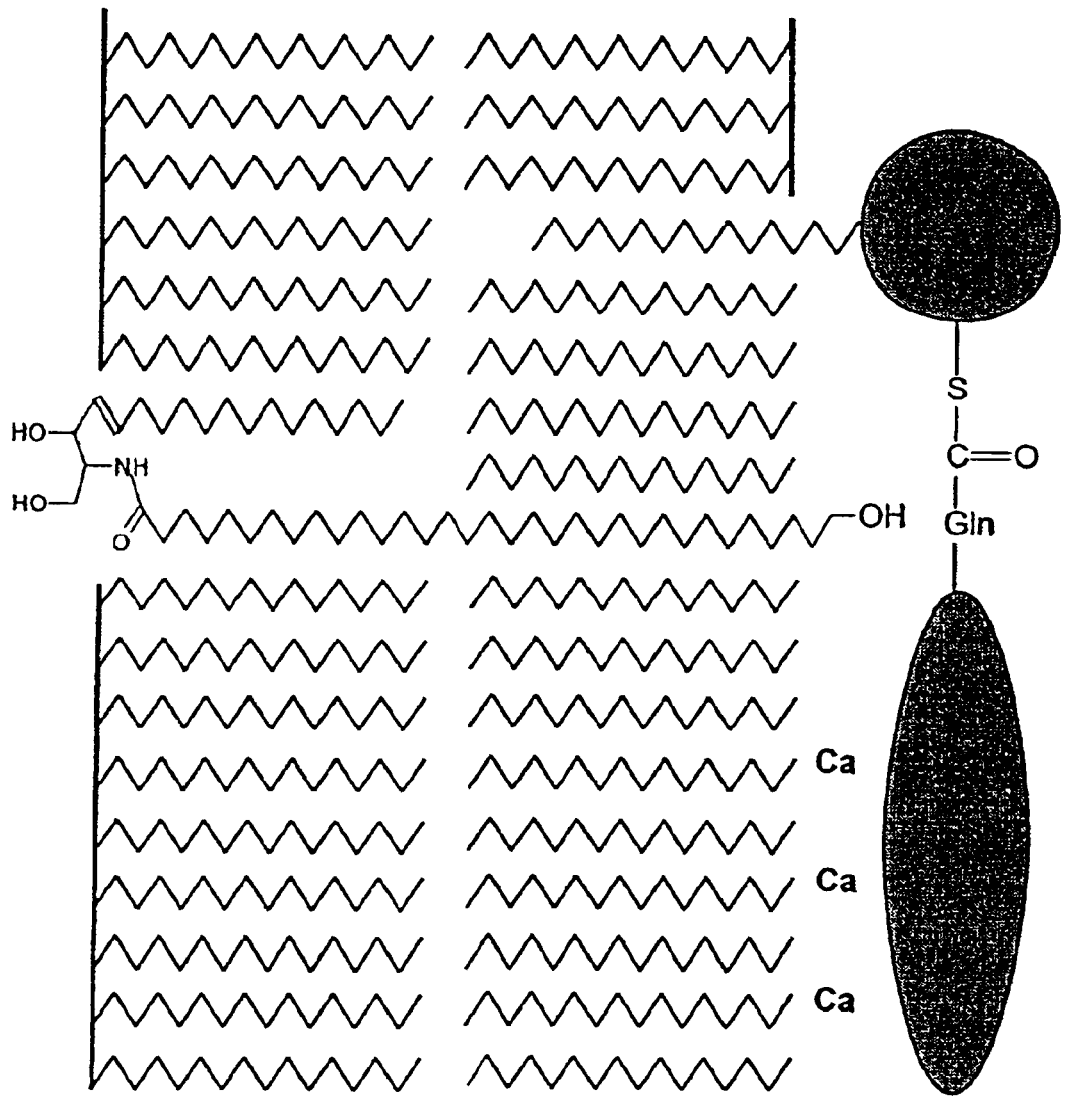
Figure 15C:
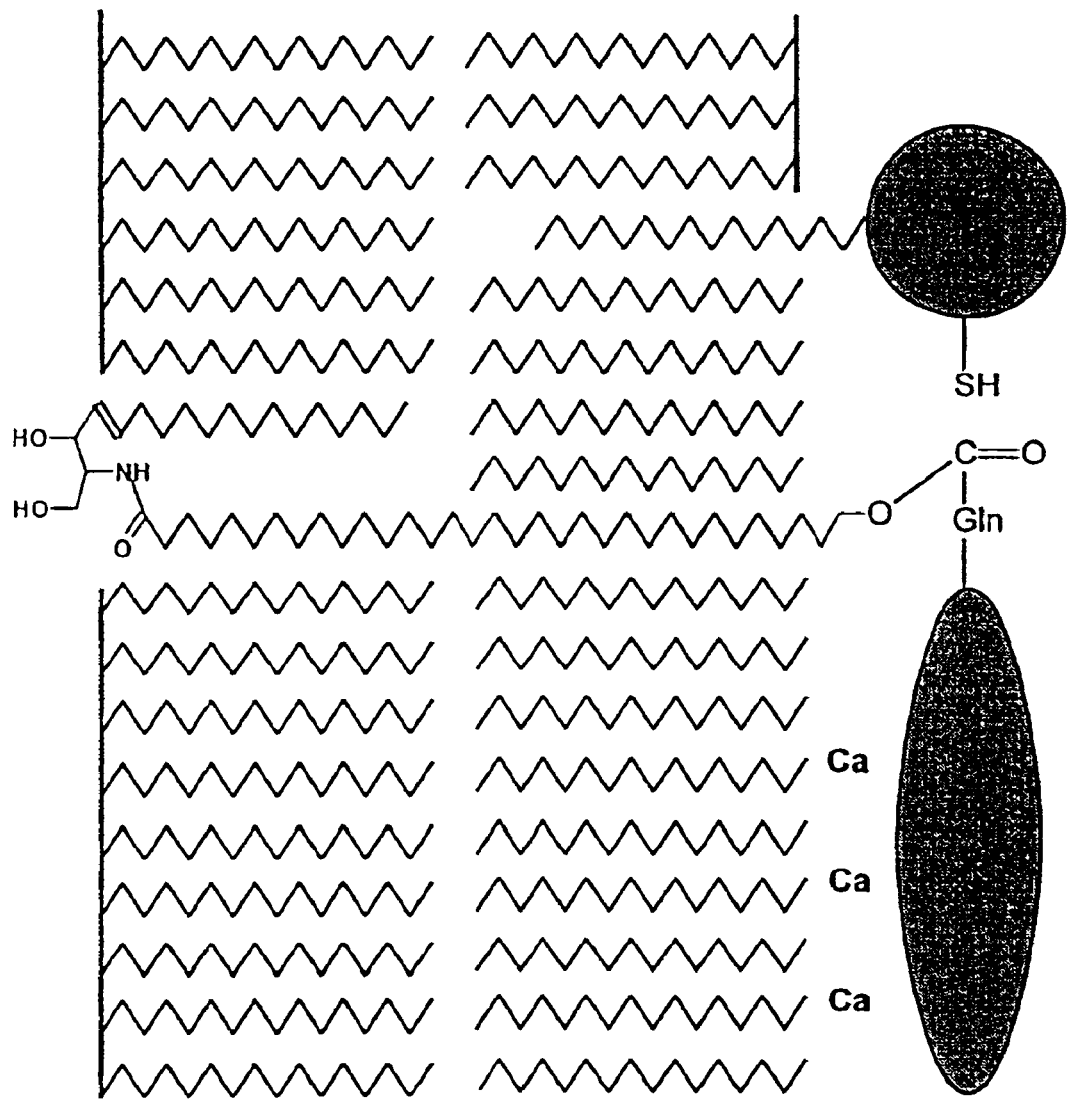

FIG. 15 Model for the Orientation and Reaction of the ω-Hydroxyl Group of Epidermal Ceramides.

(A) The TGase 1 enzyme (sphere) and involucrin (oval) are bound to the cell membrane bilayer by acyl lipid adducts or Ca$^{++}$ ions, respectively. (B) During terminal differentiation, in the presence of sufficient Ca$^{++}$, they react through a limited selection of glutamine residues. (C) The ω-hydroxyceramides (or lipid Z) can orient on membranes with the ω-OH group either facing into or out of the cell, however, only the former are esterified onto involucrin by TGase 1.

DETAILED DESCRIPTION OF THE INVENTION

Many inherited autosomal recessive ichthyoses (ARI) are caused by improper or incomplete lipid barrier function in the skin due to genetic errors of either protein or lipid synthesis. It is previously known that the mutations in the transglutaminase I gene resulting in inactive enzyme is the cause of one ARI disease termed lamellar ichthyosis. Here is disclosed that a principle function of the enzyme is to attach ceramide lipids for complete protein/lipid barrier function in the skin. The invention provides: (1) enzyme in a stable active form; (2) synthetic ceramide analogs that can function the same way as normal skin ceramides; and (3)

synthetic lipid vesicles that can stably carry both the enyzme and synthetic ceramide analog to the skin. One effect is the lipid barrier function in normal skin is improved. Another effect is that it might be applied to affected ARI skin in order to provide ameliorative therapy.

In aspects of the invention, compositions are provided that allow for the study, treatment, and prevention of skin disorders (e.g., Ichthyosis-related diseases). It has been discovered that these compositions can be used to deliver proteins (e.g., enzymes), chemicals, or other molecules to skin cells. Embodiments can comprise an enzyme (e.g., TGase 1) joined to a synthetic lipid vesicle of composition similar to eukaryotic plasma membranes (SLV) and an adaptor (e.g., involucrin). Further, embodiments of can include an enzyme (e.g., TGase 1) joined to a SLV and an adaptor (e.g., involucrin), wherein the adaptor is also joined to a delivery agent (e.g., extracellular matrix protein, CE assembly protein, enzyme, or other molecule). Additionally, some embodiments include the compositions described above further comprising a ceramide reactant (e.g., T-hydroxyceramide or lipid Z) joined to the adaptor.

Methods of identifying and manufacturing such compositions including the use of software, hardware, approaches in rational molecule design, molecular biology, and the use of biochemical assays to screen such manufactures are provided in the following disclosure. Methods of using these compositions are also embodied in aspects of the invention including the manufacture of supports having an enzyme, adaptor, and ceramide reactant for the isolation and identification of proteins involved in CE assembly and the preparation of pharmaceuticals and cosmetics for the treatment and/or prevention of skin disorders such as ichthyosis-related diseases. Methods of treatment of skin disorders such as ichthyosis-related diseases using these pharmaceuticals and cosmetics are also provided.

In the discussion below, an in vitro model system for characterizing the function of TGase 1 on the surface of synthetic lipid vesicles (SLV) of composition similar to eukaryote plasma membranes is described. Recombinant baculovirus-expressed human TGase 1 readily binds to SLV, becomes active in cross-linking above 10 $\mu$M $Ca^{++}$, in comparison to above 100 $\mu$M in solution assays, which establishes that the membrane surface is important for enzyme function. It has also been discovered that involucrin binds to SLV containing 12–18% phosphatidylserine at $Ca^{++}$ concentrations above 1 $\mu$M. In reactions of involucrin with TGase 1 enzyme in solution, 80 of its 150 glutamines serve as donor residues. However, on SLV carrying both involucrin and TGase 1, only five glutamines serve as donors, of which glutamine 496 was the most favored.

Additionally, it was discovered that the membrane-bound keratinocyte TGase 1 enzyme can perform a novel transesterification reaction between specific glutaminyl residues of human involucrin and a novel functional analog of epidermal specific $\omega$-hydroxyceramides, N-[16-(16-hydroxyhexadecyl)oxypalmitoyl] sphingosine (lipid Z). When recombinant human TGase 1 and involucrin were reacted on the surface of synthetic lipid vesicles containing lipid Z, lipid Z was attached to involucrin and formed saponifiable protein-lipid adducts. By mass spectroscopy and sequencing of tryptic lipo-peptides, the ester linkage formation utilized involucrin glutamine residues 107, 118, 122, 133 and 496 by converting the $\gamma$-carboxamido groups to lipid esters. Several of these residues have been found previously to be attached to ceramides in vivo. Mass-spectrometric analysis after acetonide derivatization also revealed that ester formation involved the $\omega$-hydroxyl group of lipid Z.

Not wanting to be limited to any particular embodiment and offered only to exemplify one possible mechanism, the following model of the CE assembly and ceramide attachment is provided. Refering to FIG. 9, expressed TGase 1 (large sphere) attaches to a cellular membrane or lipid bilayer by way of the lipid adducts on its amino-terminal portion. As the $Ca^{++}$ concentration at the micro-environment of the membrane surface rises above a critical threshold at the advent of terminal differentiation, involucrin (thin rod) attaches spontaneously. This binding is fostered through ionic interactions of multiple Glu residues of involucrin, $Ca^{++}$, and the anionic PS-rich membrane surface (thick rod). The membrane surface regulates the steric interaction of TGase 1 with involucrin and aligns specific Gln residues of involucrin near the active site of juxtaposed TGase 1 molecules. Cross-linking reactions are then initiated as the $Ca^{++}$ concentration rises. Further, the activated Gln residues are transferred to other nearby substrates including other involucrin, desmoplakin, envoplakin, etc. (small spheres), cross-linking occurs, and CE assembly is initiated. During these events, the $\omega$-hydroxyceramides (or lipid Z) orient on membranes with the $\omega$-OH group either facing into or out of the cell. (See FIG. 15(C)). The $\omega$-hydroxyceramides (or lipid Z) that face into the cell are esterified onto involucrin by TGase 1. The findings provided below demonstrate a novel role for membranes, TGase 1, involucrin, and $\omega$-hydroxyceramides (or lipid Z) in keratinocyte barrier function and provide several insights into the pathophysiology of lamellar ichthyosis resulting from TGase 1 dysfunction.

The section below describes experiments that lead to the discovery that TGase 1 can be stabilized in an SLV and can cross-link involucrin so as to make a composition comprising TGase 1 and involucrin joined to an SLV.

Involucrin Binds to SLVs Containing Physiological Concentrations of PS

Figure 1A:
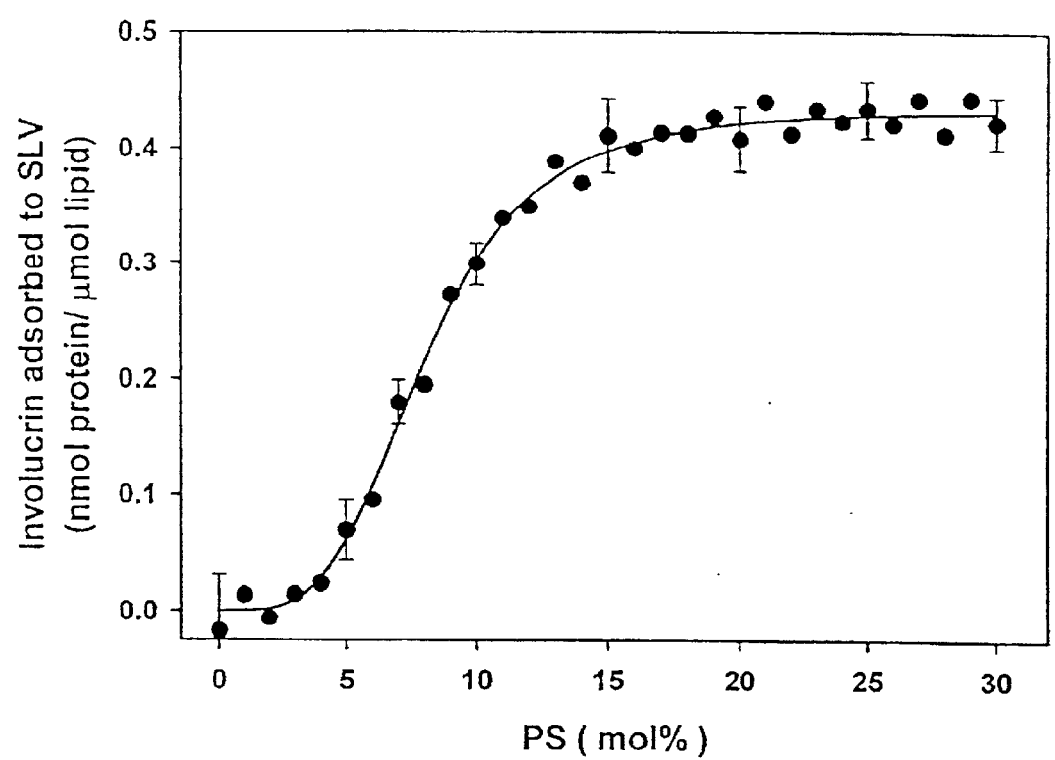
FIG. 1 The Attachment of Involucrin to SLV.

By using SLV formulations that mimic the cytoplasmic surface of plasma membranes of eukaryotic cells (Moisor, M. and R. M. Epand, *J. Biol. Chem.*, 269: 13798–13805 (1994)), it was found that involucrin readily absorbed to SLV. Accordingly, saturating amounts of involucrin (0.6 nmol protein/$\mu$mol lipid) and 1 mM $Ca^{++}$ (typical for TGase assays) were contacted with SLVs and the soluble involucrin content of the inter-SLV buffer was measured after pelleting of the SLV by ultracentrifugation. As shown in FIG. 1A, increasing the dipalmitoyl phosphatidylserine (PS) content of SLVs from 0 to 30%, in 1% increments, resulted in an increased binding of involucrin sigmiodally between 4 to 15 mol % PS and could be fitted with r=0.93 to a log (y/100–y)=3.82 log [PS %]–0.904 Hill's equation, where y is the ratio of SLV-bound involucrin to the maximal binding. (McLaughin, S. and M. Whitaker, *J. Physiol.* (London), 396: 189–204 (1988)).

Figure 1B:
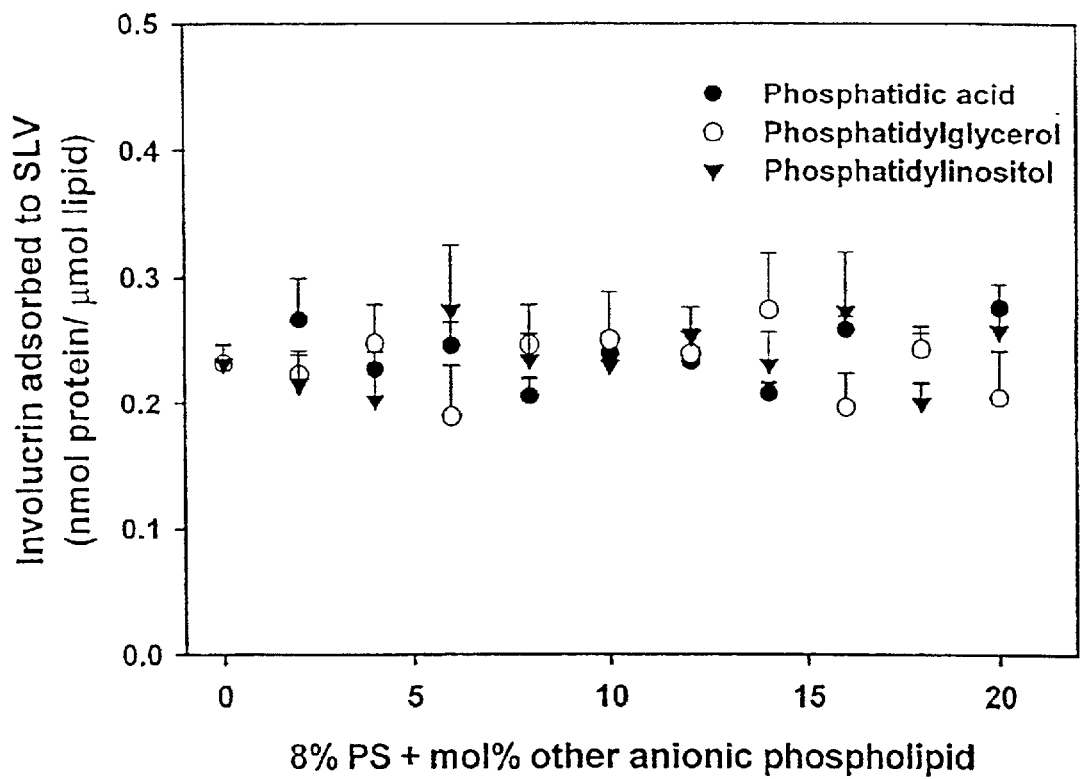

Next, SLVs containing 15–30% PS were contacted with increasing concentrations of involucrin to determine the amount of involucrin required to saturate an SLV. This experiment demonstrated that SLVs could be saturated by 0.43±0.02 nmol involucrin/$\mu$mol lipid. This amount of incorporated involucrin corresponds to about one involucrin molecule/500 $nm^2$ of surface area. Since an involucrin molecule is 46×1.5 nm (an area of approximately 70 $nm^2$), the amount of involucrin that decorates the surface of an SLV is remarkably high (approximately 15%). (Yaffe, et al., *J. Biol. Chem.*, 267: 12233–12238 (1992)). The adsorption of involucrin to the SLV was specific to PS since substitutions by phosphatidic acid, phosphatidyl glycerol, or phosphatidyl inositol did not enhance binding. (FIG. 1B).

Experiments were also conducted to determine whether a variety of other known CE substrate proteins could bind to SLV. The recombinant proteins tested included loricrin, and the small proline rich proteins 1 and 2. These proteins were unable to directly attach to SLV. (FIG. 2). Similarly, succinylated casein, a commonly used artificial substrate for amine incorporation by TGases, did not associate directly with SLV. The results from these experiments established that involucrin can bind to lipids that contain physiological concentrations of PS. Evidence that the SLV-involucrin association is mediated by $Ca^{++}$ concentration is provided in the the following section.

Involucrin Binds to SLV by a $Ca^{++}$ Ion Dependent Mechanism

The experiments described below were designed to determine the optimal free $Ca^{++}$ concentration required for the binding of saturating amounts of involucrin to SLVs containing 15 mol % PS (0.6 nmol/µmol lipid). As shown in FIG. 3, maximal binding of involucrin to SLVs occurred with >20 µM $Ca^{++}$, and half-maximal binding was estimated at 4.2±0.7 µM. Binding of involucrin to SLVs was first detected at 1:M, however. The induction of involucrin binding by $Ca^{++}$ was completely reversible when an excess of EGTA or EDTA was introduced and magnesium and monovalent ions did not support the binding of involucrin to SLVs. These results demonstrated that the association of involucrin with lipids is mediated by the concentration of $Ca^{++}$ at the lipid surface microenvironment. The experiments below reveal the discovery that TGase 1 can be stabilized and incorporated into an SLV.

Solubilized Recombinant TGase 1 Binds Spontaneously to SLV

The following provides evidence that some preparations of TGase 1 spontaneously associate with SLV. Recombinant TGase 1 enzyme that is expressed in the baculovirus system is constitutively N-myristoylated and S-myristoylated or S-palmitoylated on its amino-terminal 10 kDa portion and can be found mostly in the particulate fraction of the insect cell homogenates. (Candi, et al., *J. Biol. Chem.*, 273: 13693–13702 (1998)). Like the native enzyme expressed in epidermal keratinocytes, the recombinant TGase 1 can be solubilized from the membranes by extraction with the detergent Triton X-100, and the lipid adducts on the enzyme are retained. Alternatively, the TGase 1 can be solubilized by use of 1 M $NH_2OH$—HCl, which hydrolyses the S-acyl adducts off the enzyme. (Steinert, et al., *J. Biol. Chem.*, 271: 26242–26250 (1996), herein expressly incorporated by reference in its entirety).

The TGase 1 enzyme purified by the $NH_2OH$—HCl method is unable to bind to SLVs, as indicated by amino acid analysis of pelleted SLV mixtures and TGase assays of the resulting supernatants. In contrast, TGase 1 enzyme purified from Triton X-100 extracts spontaneously associates with SLVs, as indicated by the disappearance of detectable enzyme activity from the supernatants of pelleted SLV mixtures. Using an SLV composed of 15% PS, the saturating amount was found to be approximately 0.9 nmol of TGase 1/µmol of lipid. (FIG. 4). The binding of recombinant TGase 1 protein to SLV was not influenced by $Ca^{++}$ ions, EGTA, or SLVs prepared with varying formulations of ingredients including anionic (20% PS), neutral (only phosphatidylcholine and cholesterol) or cationic (5% stearylamine) lipids.

These findings demonstrate that the extent of constitutive myristate and palmitate modifications of the recombinant TGase 1 protein by baculovirus is sufficient to permit spontaneous anchorage onto lipid bilayers per se. In contrast, the cytosolic TGase 2 and activated TGase 3 enzymes (in a natural, unmodified form) were unable to associate with an SLV of any composition tested. (FIG. 4). These data verify that a stabilized form of TGase 1 in a SLV can be prepared. The kinetics of membrane-bound TGase 1 was analyzed next, as presented below.

Kinetic Parameters of TGase 1 Following Attachment to SLV

Kinetic parameters for $^{14}C$ putrescine incorporation by SLV carrying 0.94 pmol of recombinant TGase 1/µmol of lipid were determined at 37° C. using three different protein substrates: succinylated casein, human SPR 2 (Tarcsa, et al., *J. Biol. Chem.*, 273: 23297–23303 (1998), and human involucrin (Table 1), of which only the latter was found to attach to the SLV. (FIGS. 1A and 2). Kinetic constants for the recombinant SPR2 substrate differed only by about a two-fold increase in $K_M$ if the PS content of SLV was 0 or 15%. A similar change in $K_M$ was observed both with putrescine and succinylated casein. One possibility is that this $K_M$ increase is due to the reduced diffusional mobility of the enzyme after attachment to the SLV. Interestingly, attachment of TGase 1 to SLV drastically affected its kinetic parameters with respect to the incorporation of putrescine into the standard succinylated casein substrate, so that the $V_{max}$ was reduced by about five-fold. (Table 1). One reason for this is that a reduced access to many of the Gln residues occurs after anchorage of the enzyme. On the other hand, the $V_{max}$ value for the recombinant SPR2 substrate was almost unchanged.

Sequencing analyses revealed that of its several Gln residues, only Gln 6 was reacted by putrescine in all three of the TGase 1 enzyme formulations described in Table 1. These data are consistent with the fact that SPR2 is a much smaller and more flexible substrate with only one reactive Gln residue. The kinetic parameters for involucrin as a substrate were immeasurably low when the SLV were formulated in the absence of PS. In comparison to solubilized TGase 1 enzyme and soluble involucrin, SLV containing 15% PS yielded a 200-fold decreased $k_{cat}$ value and an approximately 40-fold decreased $K_M$. In view of the above observations for succinylated casein, these changes also reflect drastic changes in the availability of Gln residues on involucrin for reaction with putrescine.

TABLE 1

Apparent kinetic parameters for putrescine incorporation into SPR2, involucrin, and succinylated casein by 0.94 pmol membrane-bound and solubilized TGase 1*

| | $V_{max}$ pmol.min-1 | $k_{cat(putrescine)}$ min-1 | $K_{M(app)}$ $\mu M$ | $K_{cat}/K_M$ min-1.$\mu M$ |
|---|---|---|---|---|
| Solubilized TGase 1 with | | | | |
| 1. Putrescine (+1 $\mu M$ succinylated casein) | | | 221 ± 34 | |
| Succinylated casein | 12.7 ± 2.3 | 13.5 | 61.4 ± 9.2 | 220 ± 44 |
| Human SPR2 | 10.4 ± 1.7 | 11.1 | 13.2 ± 1.9 | 838 ± 107 |
| Involucrin | 482 ± 37 | 513 | 114 ± 19 | 4514 ± 1073 |
| SLV-bound TGase 1 (0% PS) with | | | | |
| Putrescine (+1 $\mu M$ Succinylated casein) | | | 397 ± 49 | |
| Succinylated casein | 3 ± 0.3 | 3.2 | 138 ± 18.6 | 23.2 ± 6 |
| Human SPR2 | 11.2 ± 1.4 | 11.9 | 25.3 ± 2.6 | 470 ± 61 |
| SLV-bound TGase 1 (15% PS) with | | | | |
| Succinylated casein | 3.2 ± 0.2 | 3.4 | 145 ± 18 | 23 ± 5 |
| Human SPR2 | 13.1 ± 1.9 | 13.9 | 22.8 ± 3 | 610 ± 87 |
| Involucrin | 2.4 ± 0.4 | 2.55 | 2.9 ± 0.4 | 879 ± 92 |

*The PS content of the SLV is shown in parentheses. $K_{M(app)}$ values pertain to the protein, $V_{max}$ and $K_{cat}$ data are that of putrescine incorporation.

TABLE 2

Glutamine Residues in Involucrin That Serve as Acryl Donors by TGase 1*

| Peak | Peptide sequence position in involucrin | Modified Q residue(s) (mol/mol) |
|---|---|---|
| Panel A: TGase 1 reaction in the absence of membranes: | | |
| 4 | 375–378 | Q375 (0.40) |
| 5 | 532–537 | Q535 (0.08) |
| 6 | 116–121 | Q117 (0.66), Q118 (0.23) |
| 7 | 122–127 | Q122 (0.25) |
| 8 | 379–384 | Q379 (0.04), Q382 (0.05) |
| 11 | 295-3-1 | Q298 (0.08) |
| 15 | 101–109 | Q106 (0.06), Q107 (0.46) |
| 16 | 165–174 and 522–531 | <u>Q168</u> or Q525 (0.09), <u>Q172</u> or Q529 (0.37) |
| 17 | 432–441 | Q439 (0.45) |
| 18 | 385–394 | <u>Q392</u> (0.32) |
| 19 | 395–404 | Q398 (0.08), <u>Q402</u> (0.39) |
| 20 | 285–294 | <u>Q288</u> (0.07), <u>Q292</u> (0.35) |
| 21 | 36–46 | Q45 (0.16) |
| 22 | 129–140 | Q132 (0.06), Q133 (0.47) |
| 23 | 69–80 | Q73 (0.04) |
| 25 | 509–521 | Q515 (0.06), Q519 (0.35) |
| 26 | 419–431 | Q419 (0.36), <u>Q425</u> (0.08), Q429 (0.39) |
| 27 | 469–481 | Q469 (0.17), Q475 (0.06), Q479 (0.42) |
| 28 | 563–575 | Q572 (0.10) |
| 29 | 405–418 | Q408 (0.07), Q412 (0.41), Q415 (0.08) |
| 31 | 150–164 | Q151 (0.30), <u>Q158</u> (0.09) |
| 32 | 486–501 | <u>Q489</u> (0.49), <u>Q495</u> (0.11), <u>Q496</u> (0.71), Q499 (0.04) |
| 33 | 442–461 | Q445 (0.09), Q449 (0.43), <u>Q455</u> (0.10), <u>Q456</u> (0.56), Q459 (0.04) |
| 34 | 324–344 | <u>Q328</u> (0.10), Q332 (0.38), Q335 (0.25), <u>Q342</u> (0.37) |
| 35 | 265–284 | Q272 (0.34), Q282 (0.45) |
| 36 | 81–100 | Q88 (0.07) |
| 38 | 538–562 | Q539 (0.42), Q551 (0.48) |
| 39 | 345–374 | Q348 (0.09), Q353 (0.33), Q363 (0.35), <u>Q368</u> (0.09), <u>Q369</u> (0.79), Q372 (0.37) |
| 40 | 175–264 | <u>Q178</u> (0.09), Q182 (0.42), <u>Q188</u> (0.08), Q192 (0.36), <u>Q198</u> (0.09), Q202 (0.37), <u>Q208</u> (0.09), Q212 (0.35), <u>Q218</u> (0.08), Q222 (0.36), Q227 (0.10), Q232 (0.29), Q238 (0.06), Q242 (0.34), Q248 (0.08), Q252 (0.35), Q258 (0.07), <u>Q262</u> (0.37) |

TABLE 2-continued

Glutamine Residues in Involucrin That Serve as Acryl Donors by TGase 1*

| Peak | Peptide sequence position in involucrin | Modified Q residue(s) (mol/mol) |
|---|---|---|
| Panel B: TGase 1 reaction with Sf9 particulate fraction: | | |
| 6 | 116–121 | Q118 (0.03) |
| 7 | 122–127 | Q122 (0.07) |
| 15 | 101–109 | Q107 (0.09) |
| 22 | 129–140 | Q133 (0.04) |
| 32 | 486–501 | Q496 (0.54) |
| Panel C: TGase 1 reaction on SLV: | | |
| 6 | 116–121 | Q118 (0.04) |
| 7 | 122–127 | Q122 (0.06) |
| 15 | 101–109 | Q107 (0.11) |
| 22 | 129–140 | Q133 (0.16) |
| 32 | 486–501 | Q496 (0.59) |

*Tryptic peptide peaks that contained $^{14}$C-putrescine label, indicated by arrows in FIG. 9, were sequenced. The location and amount of modified Gln (Q) residues were identified by the appearance and quantitation of PTH-(-glutamylputrescine (FIG. 8). Underlined residues denote those seen in in vivo cross-linking. (Steinert, P.M. and L.N. Marekov, J. Biol. Chem., 272: 2021–2030 (1997)).

Additionally, the data of Table 1 demonstrate that the kinetic constants of putrescine incorporation into involucrin by TGase 1 alter with the PS content of the SLV. As shown in FIG. 5, for example, the reaction rate follows a sigmoidal shape with a sharp increase between 6 to 11% with maximal incorporation at 10–20% PS content. This observation is to be expected from the maximal binding of involucrin to SLV and thus serves as a valid control. (FIG. 1A). Beyond 20% PS content, the efficiency of the reaction declines possibly because of inhibition of TGase 1 by excessive charge. (FIG. 5 and Table 1).

The results from the kinetic studies presented above prove that TGase 1 containing SLVs are effective enzymes. The experiments below demonstrate that the $Ca^{++}$ requirements for TGase 1 activity are lower when the enzyme is disposed on an SLV than when the enzyme is in a soluble form.

$Ca^{++}$ Requirements for TGase 1 Reaction are Lowered Following Attachment to SLV The following experiments were conducted to determine the optimal $Ca^{++}$ ion concentration for cross-linking involucrin. The optimal $Ca^{++}$ ion concentration required for the TGase 1 reaction has not been measured for any substrate. Standard in vitro solution assays contain 1–5 mM $Ca^{++}$. (Folk, J. E. and J. S. Finlayson, Adv. Protein Chem., 31: 1–133 (1977); Folk, J. E., Adv. Enzymol. Related Areas Mol. Biol., 54: 1–56 (1983); and Lorand, L. S. M. Conrad, Mol. Cell Biochem., 58: 9–35 (1984)). When solubilized recombinant TGase 1 was contacted with 1.2 nmol of involucrin in the absence of SLV, the reaction follows an apparent sigmoidal curve, with half-maximal incorporation occurring at 310±80 μM $Ca^{++}$. (FIG. 6, open symbols). However, when an equimolar amount of TGase 1 was bound to SLV containing 15% PS and saturating amounts of involucrin were added, the $Ca^{++}$ activation constant was approximately 22±1.3 μM $Ca^{++}$ (FIG. 6, closed symbols). Similar values (19±2.7 μM) were obtained for succinylated casein, a substrate that does not bind significantly to SLV. (FIG. 2). Further, when TGase 1 was attached to neutral SLV containing 0% PS, the half-maximal enzyme activity with succinylated casein was calculated at 370±110 μM $Ca^{++}$.

Together, these data demonstrate that the changes in $Ca^{++}$ sensitivity observed were reflections of the altered local $Ca^{++}$ micro-environment on PS containing bilayers, rather than an enhanced enzyme affinity towards $Ca^{++}$ or its substrates in the membrane-bound state. Although a wide range of dissociation constants of PS-$Ca^{++}$ adducts have been reported, local $Ca^{++}$ ion concentration can be much higher in the intimate proximity of PS-containing membranes, as compared to the bulk solution. (Mosior, M. R. M. Epand, Biochemistry, 32: 66–75 (1993) and McLaughin, et al., J. Gen. Physiol., 77: 445–473 (1981)). The data also demonstrate that cross-linking of involucrin by membrane-bound TGase 1 occurs at a 10-fold lower $Ca^{++}$ concentration than that required for the soluble enzyme and substrate. Moreover, comparison with the data of FIG. 3 reveals that this concentration is several-fold higher than that required for efficient involucrin binding to SLV, which thereby provides evidence of a temporal order to these processes in vivo. Evidence that the site of involucrin attachment to TGase 1 is mediated through the Gln residues of involucrin is provided below.

Solubilized Recombinant TGase 1 Reacts with the Majority of Gln Residues of Involucrin In this first set of experiments, the Gln residues of involucrin that were cross-linked by recombinant TGase 1 were analyzed in the absence of natural insect cell membranes and SLV. $^{14}$C-putrescine incorporation into involucrin was analyzed following trypsin digestion and separation of tryptic peptides on a C18 reverse phase HPLC column. Labeled peptide peaks were dried and identified by sequencing. The PTH derivative of (-glutamylputrescine isopeptide formed in the TGase reaction was identified as a distinct peak in the Porton LP 3000 gas-phase sequencer. (FIG. 7). A total of 40 tryptic peptides were reliably separated, of which 29 (arrows) were labeled by $^{14}$C-putrescine in a reaction with solubilized recombinant TGase 1 and involucrin. (FIG. 8A). Sequencing identified 80 labeled Gln residues (Table 2, panel A), with a total of about 20 mol of putrescine incorporated/mol of involucrin (Table 2, panel A). In contrast to the 29 Gln residues found to be involved in the binding of involucrin to soluble TGase 1 in the experiments above, membrane-bound TGase 1 binds to involucrin through five specific Gln residues, as discussed in the following section.

Attachment of TGase 1 to Insect Cellular Membranes or SLV Reveals Highly Specific Utilization of Gln Residues of Involucrin The experiments above were repeated using recombinant TGase 1 and involucrin bound to either the crude particulate membranes of Sf9 insect cells or SLVs. In this case, only five tryptic peptide peaks were labeled (Table 2, panel B), involving five different Gln residues. Similarly, following binding of recombinant TGase 1 and involucrin to SLVs containing 15% PS (FIG. 9B), the same five labeled tryptic peptides were recovered and identified. (Table 2, panel C).

In both experiments using membrane-bound TGase 1, approximately 1 mol of putrescine was incorporated/mol of involucrin of which Gln496 was the most brightly labeled residue. Interestingly, these data corroborate an earlier study in which Gln496 was identified as the most strongly labeled residue in a reaction of involucrin with the TGase 1 enzyme associated with crude keratinocyte membranes. (Simon, H. and H. Green, *J. Biol. Chem.*, 263: 18093–18098 (1988)). The remaining four Gln residues (Gln107, Gln118, Gln122 and Gln133) that were slightly labeled are located in the evolutionarily conserved head domain or ancestral portion of involucrin. Thus, TGase 1 joined to an SLV mediates the cross-linking of involucrin through five specific Gln residues and, thereby forms a composition comprising TGase 1 and involucrin joined to an SLV. The disclosure below decribes an approach to synthesize an anolog of T-hydroxyceramide (lipid Z), a molecule that can also join to a composition comprising TGase 1, involucrin, and SLV.

Synthesis of the ω-Hydroxyceramide Analog Lipid Z

Figure 10A:
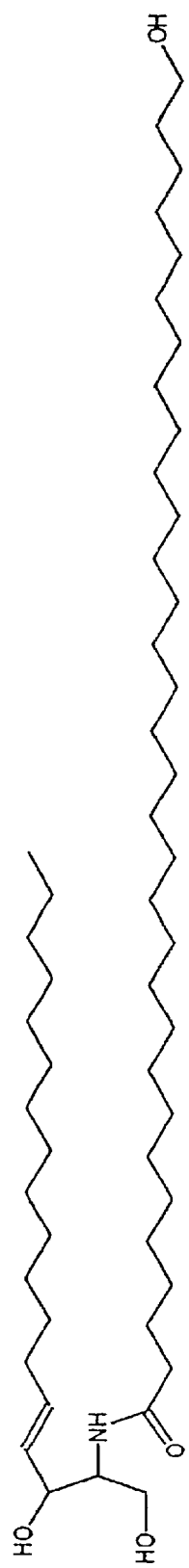
Figure 10B:
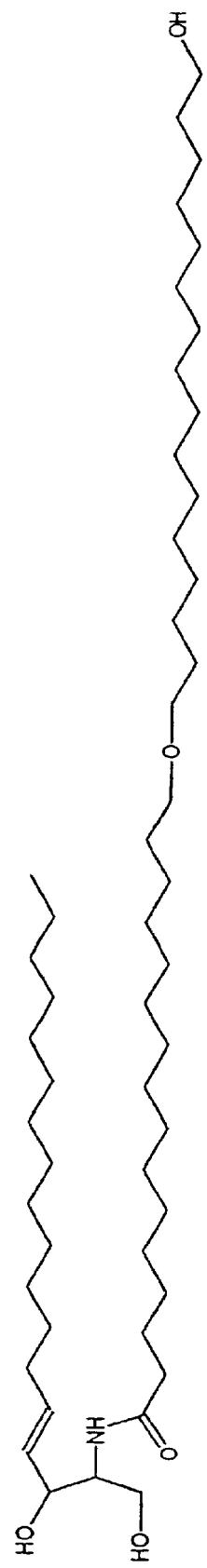

An artificial ceramide that mimics natural epidermal ceramides, called lipid Z, has been synthesized. (FIGS. 10A and B). Lipid Z is a synthetic ω-hydroxyceramide that is similar in size to natural ceramides and has overall solubility and chromatographic properties similar to pig and human epidermal ceramides. Lipid Z, 16-(16-hydroxyhexadecyl) oxyhexandecanoic acid, is similar to tetratriacontanoyl (C34) fatty acids, and has a terminal (ω) primary alcoholic functional group. This product was linked to a sphingosine base in order to create the ceramide analog. (FIG. 10B). Natural ω-hydroxyceramides (FIG. 10A) have chain lengths of >C30 and are ester-linked to CE structural proteins. (Nemes et al., *J. Biol. Chem.*, 274:11013–11021 (1999)). When present in lipid bilayers, the terminal hydroxyl group of such long acyl chain compounds span the lipid bilayer and are exposed on the side opposite the polar sphingosine moiety. The methods of synthesizing Lipid Z is detailed in Example 2. In the section below, a reaction of lipid Z with a composition having TGase 1 and involucrin joined to an SLV is described, as well as, an analysis of the lipo-peptide adducts produced by tryptic digestion of the involucrin present in the completed reaction.

Reaction of TGase 1 with Involucrin and Lipid Z on SLV and Recovery of Lipo-Peptides.

In the following, the manufacture of a composition comprising TGase 1, involucrin, and lipid Z joined to an SLV is described. First, the SLV carrier system described above was made and the TGase 1 and involucrin containing SLV was used to react with lipid Z. Human TGase 1 purified from the particulate fraction of insect cells in a baculovirus expression system was spontaneously joined to an SLV containing 15% PS by virtue of its fatty acid moieties that are post-translationally added in Sf9 insect cells. Involucrin was joined to the TGase 1 containing SLV in the presence of 1 mM $Ca^{++}$ and cross-linking was allowed to occur. Subsequently, the water-insoluble lipid Z was added to the SLV containing cross-linked TGase 1 and involucrin. After the reaction and removal of unbound lipids, the involucrin was digested with trypsin. Lipo-peptide adducts with uniquely hydrophobic properties were selectively isolated on a C4 HPLC column using highly desorbing conditions and isopropanol gradient elution. (Marekov, L. N. and P. M. Steinert, *J. Biol. Chem.*, 273: 17763–17770 (1998)). Under such conditions, free peptides do not bind to the column and only the lipo-peptides are retarded. Eluted lipo-peptides were detected by the absorption of peptide bonds at 220 nm. Five peaks were reproducibly separated from the total tryptic digest (FIG. 11), and were subjected to mass spectrometric analysis, protein sequencing and quantitation by amino acid analysis following acid hydrolysis.

Electrospray ionization mass spectrometry was used to assess the molecular weight of the isolated involucrin lipo-peptides prior to and after alkaline saponification. (FIG. 12). All five peaks displayed masses consistent with the presence of only one major detectable mass ingredient. Following a 2 hour saponification reaction, the masses of each peak decreased by 776.33 to 776.65 atomic mass units (amu), which corresponds exactly to the hydrolysis of a 794.3 Da lipid Z ester (Table 3). Mass spectrometric analysis confirmed that a composition comprising TGase 1, involucrin, and lipid Z joined to an SLV had been made. The finding that specific Gln residues of involucrin act as substrates for TGase 1-mediated esterification of involucrin and joining of lipid Z are provided in the next section.

Specific Glutamine Residues of Involucrin Serve as Substrates for TGase 1 Mediated Esterification.

To determine how lipid Z joins to the composition comprising TGase 1, involucrin, and an SLV, the involucrin lipo-peptides obtained by the approach described above were subjected to protein sequencing. Protein sequencing of each of the tryptic lipo-peptide peaks revealed a unique sequence species. Each sequence differed from the expected native involucrin sequence in that the recovered Gln residues were Glu residues. (Table 4). Four of the modified Gln residues (Gln107, Gln118, Gln122, Gln133) are located close to each other in the head domain of the protein and are preceded by a Leu residue. In three sequences where there were two consecutive Gln residues, only the second was used, that is GlnGln107,118,133Leu. A fifth Gln residue located in distant sequences toward the end of the central peptide repeating domain, was modified only to a minor extent (Gln496) and was followed by Val residue. Interestingly, three of these residues (Gln118,122,133) were identified as sites of ceramide attachment in a previous in vivo study. (Marekov, L. N. and P. M. Steinert, *J. Biol. Chem.*, 273: 17763–17770 (1998)). Thus, the same Gln residues important for assembly of the SLV, TGase 1, and involucrin complex are present in the SLV, TGase 1, involucrin, and lipid Z complex but these residues were modified. Next, the T-hydroxyl group of lipid Z was analyzed and it was discovered that this group was preferentially used in ester formation.

TABLE 3

Molecular Masses of Lipo-peptide Adducts Resolved by HPLC in FIG. 11*

| Peak | $M_r$ before Saponification (amu) | $M_r$ after | $\Delta M_r$ |
|---|---|---|---|
| 1 | 1552.14 | 775.50 | 776.64 |
| 2 | 1522.12 | 745.47 | 776.65 |
| 3 | 1833.45 | 1057.12 | 776.33 |

TABLE 3-continued

Molecular Masses of Lipo-peptide Adducts Resolved by HPLC in FIG. 11*

| Peak | $M_r$ before Saponification (amu) | $M_r$ after (amu) | $\Delta M_r$ |
|------|-----------------------------------|-------------------|--------------|
| 4    | 2218.86                           | 1442.35           | 776.51       |
| 5    | 2599.23                           | 1822.88           | 776.35       |

*Masses were deconvoluted from electrospray ionization mass spectra before and after saponification.

TABLE 4

Sequences of lipo-peptide adducts resolved by HPLC in FIG. 11*

| Peak | Sequence | Mass (amu) | Involucrin Sequence |
|------|----------|------------|---------------------|
| 1 | DQELNK (SEQ. ID. NO. 1) | 745.8 | DQQ$^{118}$LNK (SEQ. ID. NO. 6) |
| 2 | ELEEEK (SEQ. ID. NO. 2) | 775.8 | Q$^{122}$LEEEK (SEQ. ID. NO. 7) |
| 3 | AENPEQELK (SEQ. ID. NO. 3) | 1057.1 | AENPEQQ$^{107}$LK (SEQ. ID. NO. 8) |
| 4 | LDQELDQELVK (SEQ. ID. NO. 4) | 1442.7 | LDQQ$^{133}$LDQELVK (SEQ. ID. NO. 9) |
| 5 | QEAQLELPEQEVGQPK (SEQ. ID. NO. 5) | 1833.9 | AQLELPEQQ$^{496}$VGQPK (SEQ. ID. NO. 10) |

*Boldface letters indicate the modified glutamines participating in the ester formation.

The ω-Hydroxyl Group of Lipid Z is Preferentially Used in Ester Bond Formation.

In order to determine which of the three hydroxyl groups of lipid Z is used by TGase 1 in the esterification reaction, isolated lipo-peptides obtained by the approach described above were reacted under acidic conditions with dimethylacetonide and the modified lipid Z was recovered by subsequent alkaline hydrolysis. By mass spectrometry, the bulk of the lipid was converted to a product of mass of 834 amu, indicating acetonide formation of two closely juxtaposed hydroxyl groups. (FIG. 13). Such a derivative could only be formed from lipid Z if the two hydroxyls in positions 1 and 3 on the sphingosine moiety were not ester linked to the peptides. Approximately 90% of the lipid appeared as acetonide derivative by mass spectrometric analysis, whereas the rest was either not converted or hydrolyzed during processing. Similar conversion yields were obtained using free lipid Z instead of lipo-peptides, showing that complete conversion was not achievable by this method or that some acetonide was hydrolyzed during isolation. As additional controls, lipid Z was replaced with palmitoylsphingosine or 16-hydroxypalmitoylsphingosine in SLV membranes but no involucrin-adduct formation was observed, indicating that the hydroxyl group on the end of an acyl chain, which is long enough to span the lipid bilayer membrane, is sine qua non for the esterification reaction. Kinetic studies on the lipid Z esterification of involucrin by TGase 1 were then performed and the results are presented below.

Kinetics of Lipid Z Esterification of Involucrin by TGase 1.

Figures 14A, 14B, 14C:
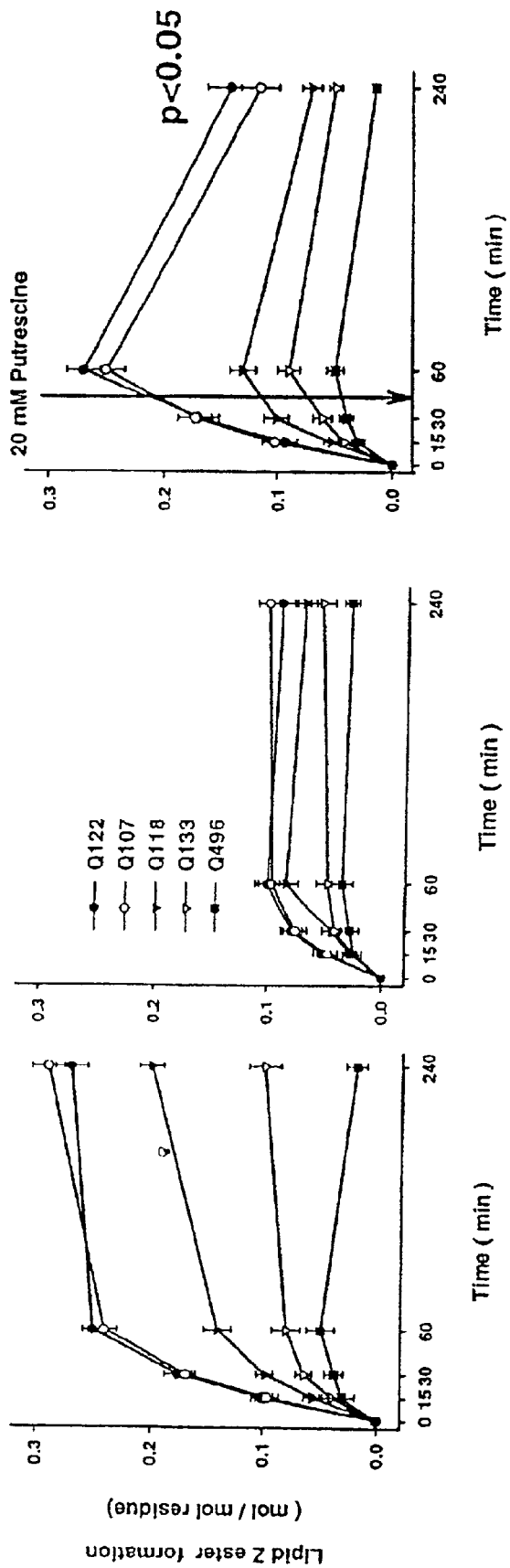

Analysis of the composition having lipid Z, TGase 1, and involucrin joined to an SLV revealed that as much as 25 mol % of the lipid Z substrate was incorporated into SLV without interference with SLV stability or binding of involucrin and TGase 1. The rate of lipid Z incorporation into involucrin remained linear up to this level indicating a high KM (>100 mol %). However, for practical reasons, SLV formulations with 1 mol % lipid Z, in which the incorporation rate was 2.2±0.3 fmol of lipid Z/s, were routinely used. Nevertheless, under all experimental conditions tested, partial esterification of the five reactive Gln residues could be obtained. (FIG. 14A). Using involucrin amounts that were determined not to saturate the binding capacity of the SLV [0.3 nmol protein/μmol lipid], a maximum of 0.1–0.3 mol of lipid ester formation was possible per mole of Gln residues 107, 118, 122, and 133, and <0.05 mol/mol for Gln 496 in the 4 h reaction. Addition of more TGase 1 enzyme did not increase the extent of esterification. In a series of controls, as expected, lipid Z esterification was completely inhibited by the presence of 5 mM EDTA or 20 mM of cystamine, a TGase active site inhibitor. (FIG. 11). Addition of up to 2% of the water-soluble primary alcohol 1-hexanol did not significantly (p=0.05) inhibit formation of lipid Z ester. Further, inclusion of 1 mM putrescine as a competitive TGase amine co-substrate inhibited ester formation of each reactive Gln residue by 2–3 fold. (FIG. 14B). Likewise, when 20 mM putrescine was added at 45 min during the reaction, there was about a two-fold and time dependent reduction in ester yields as compared to 1 h levels. (FIG. 14C). Together, these data establish that the transesterification reaction is a membrane-bound TGase 1 dependent enzyme reaction and that inhibition of TGase activity by established methods afforded direct inhibition of ester bond formation. (FIG. 11).

A Dual Role for TGAaseI

Of several enzymes likely to be involved in cross-linking reactions to form the CE barrier during terminal differentiation in stratified squamous epithelia, the TGase 1 enzyme is perhaps the most complex since it exists in multiple forms. (Steinert, et al., *J. Biol. Chem.*, 271: 26242–26250 (1996) and Kim, et al., *J. Biol. Chem.*, 270: 18026–18035 (1995)). This enzyme is of critical importance in skin barrier function in particular since mutations in its gene resulting in loss of activity cause the devastating life-threatening disease lamellar ichthyosis. (Huber, et al., *Science*, 267: 525–528 (1995); Russell, et al., *Nature Genet.*, 9: 279–283 (1995); and Parmentier, et al., *Hum. Mol. Genet.*, 5: 555–559 (1996)). Most of the TGase 1 enzyme resides on membranes through N-myristoyl and S-myristoyl or S-palmitoyl linkages although minor amounts dissociate to reside in the cytosol. (Chakravarty, R. and R. H. Rice, *J. Biol. Chem.*, 264: 625–629 (1989); Phillips, et al., *Biochemistry*, 32: 11057–11063 (1993); Steinert, et al., *J. Biol. Chem.*, 271: 26242–26250 (1996); and (Kim, et al., *J. Biol. Chem.*, 270: 18026–18035 (1995)).

TGases are well known to perform a two-step reaction first activating a protein bound glutamine residue through a thioester intermediate, followed by the transfer of the glutaminyl moiety to an acceptor amine group, usually the ε-$NH_2$ group of a protein-bound lysine residue (thereby forming an Nε(γ-glutamyl)lysine isopeptide bond) or a polyamine (Greenberg et al., *FASEB J.*, 5: 3071–3077 (1991). Typically, TGases are responsible for the crosslinking of proteins to form stable, insoluble macromolecular assemblies that are used for many purposes in biology. In some circumstances in the absence of an acceptor amine, the acyl transfer may occur onto water, resulting in deamidation of the protein bound glutamine residue. In addition, early studies have shown using model peptides that TGase 2 may also form an ester linkage by transferring the glutaminyl moiety to a primary alcohol (Gross, M. and J. E. Folk, *J. Biol. Chem.*, 249: 3021–3025 (1974) and Parameswaran, K. N. and L. Lorand, *Biochemistry*, 20: 3703–3711 (1981)), but heretofore the biological occurrence or significance of this reaction has not been demonstrated. A glutamine residue in a protein represents an intrinsically activated high free energy derivative of glutamic acid, and the release of ammonia from its γ-carboxamido group provides sufficient free energy to drive the reaction to form isopeptide or ester bonds.

In one embodiment, a physiological model system to explore the properties of the TGase 1 enzyme has been developed. The data introduce, for example, a so far unstudied catalytic cofactor, the membrane surface, that regulates the interaction of membrane-bound TGase 1 enzyme and its substrates. It was also found that involucrin also binds to SLV membranes of similar PS content to those of the cytoplasmic surface of plasma membranes of eukaryote cells. (Hauser, H. and G. Poupart, *The Structure of Biological Membranes*, Yeagle, P., ed., pp. 3–73 (1991)). The data discussed above provide evidence that the residue specificity of the TGase 1 reaction is dependent on the attachment of itself and involucrin to the membrane surface. (See e.g., FIG. 9). These observations have important implications for the mechanism of assembly of the CE barrier structure in stratified squamous epithelia.

Optimized involucrin cross-linking by membrane-bound TGase 1 is largely dependent on the ingredients of the membrane and requires $Ca^{++}$ ions and PS, an inherent constituent of the cytoplasmic face of membranes in living eukaryote cells. (Hauser, H. and G. Poupart, *The Structure of Biological Membranes*, Yeagle, P., ed., pp. 3–73 (1991)). PS is required for a number of other physiological processes, where $Ca^{++}$-dependent binding of proteins to cell membranes is a condition that facilitates enzyme activity, as exemplified in case of protein kinase C activation or blood clotting. (Moisor, M. and R. M. Epand, *J. Biol. Chem.*, 269: 13798–13805 (1994); Lee, M-H and R. M. Bell, *J. Biol. Chem.* 264: 14797–14805 (1989); and (Thompson, J. M. and L. Poller, *Blood Coagulation and Haemostasis*, Thompson, J. M., ed., pp. 301–339 (1985)). As for these two well studied processes, it was found that the activating properties of PS were not substitutable by other natural anionic phospholipids, presumably because both the carboxyl and amino groups are required for sequestration of $Ca^{++}$ ions on the membrane surface.

Several studies have examined total $Ca^{++}$ concentrations in keratinocytes. Available evidence suggests there is a $Ca^{++}$ concentration gradient in the epidermis, for example, from a low level in basal cells that gradually increases toward the granular layer. (Forslind, et al., *Scanning Microscop.*, 2: 755–759 (1984)). In addition, $Ca^{++}$ concentrations are indirectly known to be much higher on cell membrane surfaces. (Menon, et al., *J. Invest. Dermatol.*, 84: 508–512 (1985)). In keratinocytes grown in submerged cultures in low $Ca^{++}$ medium, under which conditions they do not embark on terminal differentiation, net intracellular $Ca^{++}$ concentrations are about 50–100 nM. (Li, et al., *Cell Growth Differ.*, 6: 1171–1184 (1995)). When cells are grown in higher $Ca^{++}$ medium (0.5–1.5 mM), net intracellular $Ca^{++}$ levels rise briefly to about 100–200 nM and the stratification and the terminal differentiation program proceeds. (Li, et al., *Cell Growth Differ.*, 6: 1171–1184 (1995) and (Hennings, et al., *Cell*, 19: 245–254 (1980)). Similarly, normalization of a $Ca^{++}$ gradient is essential for terminal differentiation and improved barrier function in reconstructed cultured epidermis. (Vicanova, et al., *J. Invest. Dermatol.*, 111: 97–106 (1998)). However, researchers have not been able to measure the micro-environmental $Ca^{++}$ concentration at or near the membrane surface.

Typically, involucrin is expressed in mid-late spinous layers in the epidermis (or comparable levels in other stratified squamous epithelia), and is expressed early in cultured keratinocytes as elevated environmental $Ca^{++}$ levels initiate terminal differentiation. (Vicanova, et al., *J. Invest. Dermatol.*, 111: 97–106 (1998)). The TGase 1 enzyme is expressed to a minor extent in basal keratinocytes, but its major expression program approximately coincides with that of involucrin in differentiating keratinocytes. (Pillai, et al., *J. Cell Physiol.*, 143: 294–302 (1990)). The data described herein demonstrate that involucrin begins to associate onto SLV above at Ca++ concentrations above 1 µM. (See e.g., FIG. 3). These observations favor the view that involucrin binds to the plasma membranes shortly after its expression. Furthermore, the data demonstrate that the cross-linking of involucrin does not begin until the net $Ca^{++}$ concentration rises about 10-fold higher than that required for involucrin binding. (See e.g., FIG. 6). Thus, involucrin substrate and TGase 1 enzyme can remain in close juxtaposition on cellular membranes until local $Ca^{++}$ concentrations rise above a threshold level. Accordingly, together with available in vivo data, the results disclosed herein verify that a $Ca^{++}$ gradient not only orchestrates the expression of differentiation specific genes but also creates an environment required for the initiation of CE barrier formation by juxtaposed attachment of involucrin and TGase 1 to membranes for their subsequent cross-linking. (See e.g., FIG. 9). (Simon, M., *The Keratinocyte Handbook*, Leigh, et al., eds., pp. 275–292 (1994); Watt, F. M. and H. Green, *J. Cell Biol.*, 90: 738–742 (1981); and Hennings, et al., *Cell*, 19: 245–254 (1980)).

The experiments described herein also showed that the in vitro cross-linking of involucrin by TGase 1 in solution is an efficient process (Table 1) involving the utilization of more than half of the total Gln residues of involucrin. (See e.g., FIG. 8 and Table 2). Published data has identified 27 Gln residues that are used for cross-linking in vivo, 23 of which were used in the in vitro experiments described herein (See e.g., Table 2 and Steinert, P. M. and L. N. Marekov, *J. Biol. Chem.*, 272: 2021–2030 (1997)). It is plausible that the 80 Gln residues identified as being involved in cross-linking are the most available for reaction on involucrin. It is also unlikely that the utilization of multiple Gln residues was due to degradation or denaturation of involucrin. (Simon, H. and H. Green, *J. Biol. Chem.*, 263: 18093–18098 (1988); and Etoh, et al., *Biochem. Biophys. Res. Commun.*, 136: 51–56 (1986)). Conversely, the data supports the belief that involucrin can be cross-linked in vivo by soluble TGases, including perhaps the minor cytosolic forms of TGase 1. Surprisingly, more than 50% of the TGase 1 reaction involved the single Gln496 residue, of bound involucrin. Moreover, this specificity was observed for both crude insect membranes, as well as, SLV of several confections, provided that the PS content exceeded 5%. Interestingly, this residue was identified as the most reactive in an earlier in vitro study (Simon, H. and H. Green, *J. Biol. Chem.*, 263: 18093–18098 (1988)). The data described herein also demonstrate that the stereochemistry of binding of intact involucrin and subsequent cross-linking by bound TGase 1 are important determinants of this specificity.

The kinetic data of Table 1 shed light on the high degree of specificity of Gln utilization. The lowered $K_{cat}$ and $K_M$ values of membrane bound TGase 1 using bound involucrin as substrate may be due to the restriction of available Gln residues for the reaction. Further, the maximal reaction velocity can be limited by: (i) the quantity of involucrin molecules attached to a unit of membrane surface; (ii) the lateral diffusion rate of enzyme and substrate along the membrane surface; and (iii) the rate of exchange between soluble and membrane-attached involucrin. Alternatively, association with the SLV membranes can change the conformation and thus specificity of TGase 1. In control experiments (Table 1), no change in substrate specificity to the SPR2 substrate was found. Furthermore, in the insect membrane or SLV reactions only five Gln residues were used to insert about 1 mol of putrescine/mol of involucrin, of which Gln496 was the most labeled. In contrast 80 Gln residues were labeled in the soluble reaction to insert about 20 mol/mol of putrescine. Thus, the overall kinetic efficiency and selection for Gln496 was at least two-fold higher than that of the average Gln residue in a solution reaction. Thus, these five residues, and Gln496 in particular, are favorably aligned with respect to the active site of the neighboring bound TGase 1 enzyme.

It has also been documented that involucrin is cross-linked in vivo to a variety of structural proteins, including in particular desmoplakin at the site of desmosomes, envoplakin and perhaps periplakin located primarily on plasma membranes between desmosomes, as well as to itself. Further, the predominant cross-linking site with desmoplakin is through Gln496 of involucrin. (Steinert, P. M. and L. N. Marekov, *J. Biol. Chem.*, 272: 2021–2030 (1997)). Thus, some embodiments include compositions comprising TGase 1, involucrin, and lipid Z (or a functional equivalent) joined to an SLV further comprising a protein involved in CE maintenance or assembly or both. Additionally, models of the three dimensional structures of wild-type and mutant involucrin and TGase 1 proteins can be created and this information can be compared to the results from functional assays (e.g., the "cross-linking and esterification assays", described herein) so as to learn more about the early steps of CE assembly. Approaches to conduct such studies are provided in following sections.

Recently, it has been realized that ω-hydroxyceramides with long (C28–C36) fat chains as well as sphingosine moieties (C18–C22), unique in biology to mammalian epidermis, are ester-linked to glutamine and glutamate residues of a number of CE structural proteins, most notably involucrin. (Marekov, L. N. and P. M. Steinert, *J. Biol. Chem.*, 273: 17763–17770 (1998)). In this way, such ceramides contribute to lipid envelope barrier function to the epidermis. Long chain ceramides are insoluble in an aqueous environment but can be dissolved in SLV and presumably cellular membranes. Accordingly, it is plausible that the enzyme(s) required for the esterification reaction that joins involucrin to ω-hydroxyceramides or sphingosine moieties is physically located at the membrane surface so that either the ω-hydroxyl group of the acyl chain or sphingosine hydroxyl groups (or both) are in close proximity to the CE structural proteins including involucrin.

The data presented above establishes that a membrane-bound form of the TGase 1 enzyme is capable of forming ester linkages between ceramides and involucrin. By reacting a composition comprising TGase 1 and involucrin joined to an SLV with a synthetic ceramide (lipid Z) having dimensions and a chemistry typical of epidermal specific ω-hydroxyceramides, a composition comprising TGase 1, involucrin, and lipid Z joined to the SLV has been created. The synthesis of a ceramide of sufficient length has posed a daunting problem, especially since it was technically unfeasible to synthesize or isolate large quantities of natural skin ceramides, and ω-hydroxyl derivatives of fatty acids longer than tetracosanoic (C24) have not been reported elsewhere in organic chemistry. Thus, a lipid Z with an ether derivative of an ω-hydroxyacyl chain having a net length equivalent approximately to a naturally occurring epidermal C34 ceramide was synthesized. Using the SLV carrier system described herein, the TGase 1 enzyme catalyzed the formation of an ester link between lipid Z and involucrin. Notably, other soluble TGases were not caspable of this transesterification reaction onto involucrin using a variety of experimental conditions.

It should be noted that the amine cosubstrate putrescine could reduce the rate of ester formation as expected (FIG. 14B), and caused detectable decay of ester products with time (FIG. 14C). This phenomenon can be attributed to aminolysis of ester bonds by putrescine. This can occur if the conversion of the thioacyl enzyme intermediate into an ester bond is an effectively reversible process, and the amine can deplete the acyl-enzyme intermediate due to its lower free energy. This means that ester bonds formed on involucrin can be susceptible to aminolysis by lysines on proteins, resulting in the formation of the more stable (lower free energy) 'classical' Nε(γ-glutamyl)lysine isopeptide crosslink.

The experiments described herein have revealed that five different Gln residues of involucrin were esterified with high specificity and modest efficiency (FIG. 12, Table 3). Four of these are located in the phylogenetically ancient head domain of involucrin of which Gln107,118,122 have been highly conserved in dog, rat, pig and human. (Green, H. and P. Djian, *Mol. Biol. Evol.*, 9: 977–1017 (1992)). Moreover, three of the residues (Gln118,122,133) are involved in cross-linking to TGase 1. These observations support the finding that the head domain of involucrin has been evolutionarily conserved because several of its Gln residues are favorably aligned for ceramide attachment. Moreover, it undercores the fact that the in vitro SLV system described herein is a valid experimental model to study this process.

A minor reaction of Gln496 located in distant repeating sequences in the evolutionarily more recent part of involucrin was also observed. However, the low yield of esterification of Gln496 in vitro contrasts with its near quantitative utilization for amine attachment. While the stoichiometry of esterification in vitro was low (FIG. 14), direct information on the efficiency with which these residues are labeled in vivo is not yet available. However, assuming that the dimensions of involucrin are 45×1.5 nm (Yaffe et al., *J. Biol. Chem.*, 267: 12233–12238 (1992)) and a monomolecular layer on the cell periphery forms, (Jarnik et al., *J. Cell Sci.*, 111: 1051–1060 (1998)), and based on our earlier estimate of one ceramide moiety per 40 $nm^2$ (Marekov, L. N. and P. M. Steinert, *J. Biol. Chem.*, 273: 17763–17770 (1998)), there is about 2 mol of ceramide/mol of involucrin. Thus, for steric reasons each of the several potentially reactive Gln residues is likely to be labeled substoichiometrically in vivo. Previous in vivo analysis has also identified other head domain Gln residues of involucrin that were determined to lack esterification in the present study. These residues may be labeled by other processed forms of the membrane anchored TGase 1 enzyme, or other TGases. Ceramide esterification of Gln residues of the other cell peripheral CE proteins such as envoplakin and periplakin, as seen in vivo, can be replicated in our system by using the methods described herein.

Epidermal specific ceramides have C28–36 acyl chains that are long enough to span a plasma membrane bilayer, so that the ω-hydroxyl group can be located on the side opposite of the more hydrophilic sphingosine moiety. The ω-hydroxyl group of lipid Z, equal in length to the thickness of a lipid bilayer membrane, was specifically utilized for esterification to involucrin, whereas an ω-hydroxyceramide with C16 fat chain was not. Thus, in several embodiments, the ceramide is attached to a limiting membrane bilayer before it is utilized. Further, the ω-hydroxyl, rather than the sphingosine hydroxyls, was specifically utilized for ester bond formation (FIG. 13), proving that the polarity in the membrane is important. Interestingly, these data concord well with the results from other studies that in vivo ω-hydroxyglucosyceramides become ester linked through their ω-hydroxyl group before deglycosylation of their sphingosine moieties. (Doering et al., *FEBS Lett.*, 447: 167–170 (1999), Doering et al., *J. Biol. Chem.*, 274: 11038–11045 (1999); and Uchida et al., *J. Invest. Dermatol.*, 112: 543 (1999)). In this way, the ω-hydroxyl group on the outer surface of cellular membranes is accessible for esterification by the TGase 1 enzyme onto adjacent involucrin and the other early CE or membrane constituents such as envoplakin and periplakin. (FIG. 15). Thus, the reaction can proceed until a monomolecular layer becomes attached to the proteins. These events are believed to occur during late stages of terminal differentiation and cell death, perhaps corresponding to the uppermost granular cell coincident with the extrusion of lamellar body contents. In this case, the ceramide lipid envelope is attached before completion of protein envelope assembly involving massive deposition of loricrin and small proline rich proteins.

It is to be expected that perturbation of lipid envelope formation involving ceramide attachment interferes with complete CE assembly and also with the organization of the intercellular lamellae. The consequence of this disruption is an ichthyosis-related disease resulting from the diminished barrier function. (Williams, M. L. and P. M. Elias, *Dermatol. Clin.*, 5: 155–178 (1987); Traupe, H., *The Ichthyoses: A Guide to Clinical Diagnostics*, Genetic Counseling and Therapy, (1989); and Anton-Lamprecht, I., *Diagnostic Ultrastructure of Non-neoplastic Diseases*, Papadimitrou et al., eds., pp. 459–551 (1992)). An interuption of CE assembly can occur by the inability to correctly synthesize the ceramide lipids as in Refsum's disease [phytanic acid accumulation owing to phytanoyl-CoA hydroxylase deficiency (Jansen et al., *Nature Genet*, 17: 190–193 (1997))] and Sjögren-Larsson's syndrome [pathological lipid metabolism owing to fatty aldehyde dehydrogenase deficiency (De Laurenzi et al., *Nature Genet*, 12: 52–57 (1996))]. Alternatively, it could occur by the inability to correctly attach the ceramides. Notably, loss of TGase 1 activity causes the devastating life threatening disease lamellar ichthyosis. (Russell et al., *Nature Genet*, 9: 279–283 (1995); Huber et al., Science, 267: 525–528 (1995)).

The observations discussed above indicate that a novel yet essential role of the TGase 1 enzyme is to attach ceramides. The expected diminution of barrier function is consistent with the clinical and pathological observations of the human disease, as well as in the mouse knockout model (Matsuki et al., *Proc. Natl. Acad. Sci. USA*, 95: 1044–1049 (1998)). Interestingly, pathology of lamellar ichthyosis is largely restricted to the epidermis and its appendages that form lipid envelopes: internal stratified squamous epithelia that normally do not make lipid envelopes yet express abundant levels of TGase 1 for the formation of their protein envelope CE structures, are not notably affected. (Traupe, H., *The Ichthyoses: A Guide to Clinical Diagnostics, Genetic Counseling and Therapy*, (1989); Anton-Lamprecht, I., Diagnostic Ultrastructure of Non-neoplastic Diseases, Papadimitrou et al., eds., pp. 459–551 (1992); Huber et al., Science, 267: 525–528 (1995); and Williams, M. L., *Semin. Dermatol.*, 11: 169–175 (1992)). Thus, it is plausible that the severity of the LI phenotype is contributed by the inability of the TGase 1 enzyme to assemble both the lipid envelope by ester bond formation and protein envelope by cross-link bond formation.

Biochemical Embodiments

Several compositions that comprise a stabilized form of an enzyme in a synthetic lipid vesicle that can both cross-link glutamine rich molecules, such as involucrin, and mediate the formation of an ester link to hydroxyceramides, such as lipid Z, have been created. Preferred embodiments include TGase 1 (the "enzyme") joined to an SLV, TGase 1 and involucrin (the "intermediate" or "enzyme and adaptor") joined to an SLV, and TGase 1, involucrin, and lipid Z (the "product" or "enzyme, adaptor, and ceramide reactant") joined to an SLV. However, other enzymes, intermediates, and products joined to an SLV are considered equivalents of the compositions embodied herein in so far as they have been produced by or have the ability to both cross-link glutamine rich molecules (e.g., involucrin) and mediate the formation of an ester link to hydroxyceramides. That is, the "enzymes" can be characterized by their ability to form an isopeptide bond by transfer of an amine on to a glutaminyl residue of a protein and the "adaptor" can be characterized by the ability to join to an enzyme and a ceramide.

For example, mutant forms of TGase family members and proteins that share homology to domains of TGase members that can both cross-link glutamine rich molecules and catalyze the formation of an ester bond to hydroxyceramides can be "enzymes" for the purposes of this disclosure. Similarly, proteins homologous to involucrin, mutant forms of involucrin, wild-type or mutant forms of proteins involved in the assembly of the CE (e.g., trichohyalin, elafin, repetin, periplakin, desmoplakin, envoplakin, keratin intermediate filaments, members of the small proline rich family, cystatin α, and loricrin) and other proteins or peptidomimetics created to function like involucrin can be "adaptors" for the purposes of this disclosure. Further, lipids similar in structure or function to lipid Z that can be joined to the intermediate by esterification can be "ceramide reactants".

In some embodiments, the product not only comprises an enzyme, adaptor, and a ceramide reactant joined to an SLV but further comprises another molecule joined to the adaptor. As discussed above, adaptors such as involucrin have several glutamine residues that are not involved in cross-linking to a membrane-bound TGase 1 but can cross-link to solublized TGase 1. These available glutamines can also be cross-linked to drugs or cosmetics (e.g., chemicals, peptidomimetics, or proteins, such as fatty aldehyde dehydrogenase, cholesterol sulfatse, extracellular matrix proteins, pigments, and proteins involved in CE assembly). Other residues on the adaptor can also be used to join chemicals, peptidomimetics, and proteins as will be apparent to one of skill in the art including hydroxy, amino, and sulpher residues. Additionally, adaptor-fusion proteins can be constructed. For example, a fusion protein comprising avidin or streptavidin joined to involucrin can be made using techniques in molecular biology and biotinylated proteins or peptidomimetics can be joined to the fusion protein. Many molecules can be joined to adapters (referred to as "delivery agents") by a number of techniques that will be apparent given this disclosure. Desirably, delivery agents are joined to adaptors prior to the assembly of the adaptor with the enzyme. Preferred delivery agents include, but are not limited to, proteins associated with skin cells (e.g., trichohyalin, elafin, repetin, periplakin, desmoplakin, envoplakin, keratin intermediate filaments, members of the small proline rich family, cystatin α, loricrin, extracellular matrix proteins, fatty aldehyde dehydrogenase, cholesterol sulfatase, extracellular matrix proteins, and pigments). However, any protein involved in CE assembly and any chemical or peptidomimetic that can be joined to an adaptor can be a delivery agent for the purposes of this disclosure. Thus, some compositions of the invention comprise an enzyme (e.g., TGase 1), an adaptor (e.g., involucrin), a delivery agent (e.g., extracellular matrix protein), and a ceramide reactant (e.g., lipid Z). These compositions can be used to deliver a therapeutic, prophylactic, or cosmetic molecule to skin cells.

Additionally, in the experiments presented above, several different compositions of synthetic lipid vesicles have been analyzed for their ability to join with enzymes and adaptors. Preferred synthetic lipid vesicles are described throughout this disclosure, however, many other formulations of synthetic lipid vesicles that have the ability to join an enzyme and adaptor and allow for the assembly of a ceramide reactant can be created. Thus, the term "synthetic lipid vesicle" or "SLV" refers to a lipid vesicle that has these properties. In some contexts, embodiments are referred to as "carrier systems" because they can deliver the enzyme (e.g., TGase 1), adaptor (e.g., involucrin), and ceramide reactant (e.g., lipid Z) to the lipid layer of a cell through fusion of the SLV with the cell. Further, "carrier systems" refer to a composition that can deliver the enzyme (e.g., TGase 1), adaptor (e.g., involucrin), delivery agent (e.g., extracellular matrix protein), and ceramide reactant (e.g., lipid Z) to the lipid layer of a cell through fusion of the SLV with the cell. The term "carrier system" also refers to the compositions described above, wherein the SLV is replaced by a support, as described below, that can fuse with the lipid layer of a cell. The carrier systems described herein can be used as biotechnological tools to study the assembly of the CE and can be incorporated into pharmaceuticals or cosmetics for the treatment or prevention of ichthyosis-related diseases and other skin disorders. The following section describes, several software and hardware embodiments, as well as, computational methods that can be used to identify enzymes and adaptors for use in the aforementioned compositions.

Software Embodiments

The TGase 1 and involucrin nucleic acid sequence and/or the TGase 1 and involucrin protein sequence or fragments thereof can be entered onto a computer readable medium for recording and manipulation. It will be appreciated by those skilled in the art that a computer readable medium having the TGase 1 and/or involucrin nucleic acid sequence and the TGase 1 and involucrin protein sequence or fragments thereof are useful for the determination of homologous sequences, structural and functional domains, and the construction of protein models. The utility of a computer readable medium having the TGase 1 and involucrin nucleic acid sequence and/or the TGase 1 and involucrin protein sequence or fragments thereof includes the ability to compare the sequence, using computer programs known in the art, so as to perform homology searches, ascertain structural and functional domains and develop protein models so as to develop mutant forms of TGase 1 and/or involucrin proteins that can more effectively function for their intended purpose in the carrier systems and compositions described above.

The TGase 1 and involucrin nucleic acid sequence and/or the TGase 1 and involucrin protein sequence or fragments thereof can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on computer readable medium to generate manufactures comprising the nucleotide or polypeptide sequence information of this embodiment.

A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media can be a hard disc, a floppy disc, a magnetic tape, zip disk, CD-ROM, DVD-ROM, RAM, or ROM as well as other types of other media known to those skilled in the art. The computer readable media on which the sequence information is stored can be in a personal computer, a network, a server or other computer systems known to those skilled in the art.

Embodiments include systems, particularly computer-based systems that contain the sequence information described herein. The term "a computer-based system" refers to the hardware, software, and any database used to analyze the TGase 1 and involucrin nucleic acid sequence and/or the TGase 1 and involucrin protein sequence or fragments thereof. The computer-based system preferably includes the storage media described above, and a processor for accessing and manipulating the sequence data. The hardware of the computer-based systems of this embodiment comprise a central processing unit (CPU) and a data database. A skilled artisan can readily appreciate that any one of the currently available computer-based systems are suitable.

In one particular embodiment, the computer system includes a processor connected to a bus which is connected to a main memory (preferably implemented as RAM) and a variety of secondary storage devices, such as a hard drive and removable medium storage device. The removable medium storage device may represent, for example, a floppy disk drive, a compact disk drive, a magnetic tape drive, etc. A removable storage medium, such as a floppy disk, a compact disk, a magnetic tape, etc. containing control logic and/or data recorded therein (e.g., TGase 1 and involucrin nucleic acid sequence and/or the TGase 1 and involucrin protein sequence or fragments thereof) can be inserted into the removable storage device. The computer system includes appropriate software for reading the control logic and/or the data from the removable medium storage device once inserted in the removable medium storage device.

The TGase 1 and involucrin nucleic acid sequence and/or the TGase 1 and involucrin protein sequence or fragments thereof can be stored in a well known manner in the main memory, any of the secondary storage devices, and/or a removable storage medium. Software for accessing and processing the TGase 1 and involucrin nucleic acid sequence and/or the TGase 1 and involucrin protein sequence or fragments thereof (such as search tools, compare tools, and modeling tools etc.) reside in main memory during execution.

As used herein, "a database" refers to memory that can store nucleotide or polypeptide sequence information, protein model information, and information on other peptides, chemicals, peptidomimetics, and other agents that interact with enzymes, adaptors, intermediates, ceramide reactants, and products. Additionally, a "database" refers to a memory access component that can access manufactures having recorded thereon nucleotide or polypeptide sequence information, protein model information, and information obtained from the various assays ("carrier system characterization assays") provided herein including binding information, Ca++ requirements, SLV compositions, cross-linking data, $^{14}$C-putrescine incorporation, appearance of (-glutamylputrescine, HPLC elution profiles, mass spectrometric data, lipo-peptide adduct information, and the effects of molecules that inhibit or enhance ("modulate") the association of the compositions described herein. In some embodiments, a database stores the information described above for numerous different enzymes, adaptors, intermediates, ceramide reactants, and products so that a comparison of the data can be made. That is, databases can store this information as a "profile" for each molecule tested and profiles from different molecules can be compared so as to identify functional and structural characteristics that are needed in a derivative molecule to produce a desired response. Then these derivative molecules can be made by conventional techniques in molecular biology and protein engineering and tested in further rounds of functional assays.

The sequence data can be stored and manipulated in a variety of data processor programs in a variety of formats. For example, the sequence data can be stored as text in a word processing file, such as MicrosoftWORD or WORDPERFECT, an ASCII file, a html file, or a pdf file in a variety of database programs familiar to those of skill in the art, such as DB2, SYBASE, or ORACLE. A "search program" refers to one or more programs that are implemented on the computer-based system to compare a nucleotide or polypeptide sequence with other nucleotide or polypeptide sequences and the molecular profiles created as described above. A search program also refers to one or more programs that compare one or more protein models to several protein models that exist in a database and one or more protein models to several peptides, peptidomimetics, and chemicals which exist in a database. A search program is used, for example, to compare regions of the TGase 1 and involucrin nucleic acid sequence and/or the TGase 1 and involucrin protein sequence or fragments thereof that match sequences in nucleic acid and protein data bases so as to identify homologies and structural or functional motifs.

A "retrieval program" refers to one or more programs that are implemented on the computer based system to identify a homologous nucleic acid sequence, a homologous protein sequence, or a homologous protein model. A retrieval program is also used to identify peptides, peptidomimetics and chemicals that interact with a nucleic acid sequence, a protein sequence, or a protein model stored in a database. Further a retrieval program is used to identify a profile from the database that matches a desired property in a molecule.

The next section describes several methods of molecular modeling, combinatorial chemistry, and rational molecule design for the identification of more molecules that structurally or functionally resemble TGase 1 and involucrin protein sequence or fragments thereof. These molecules can also be incorporated in the carrier systems described herein.

Methods of Rational Molecule Design

Combinatorial chemistry is the science of synthesizing and testing compounds for bioactivity en masse, instead of one by one, the aim being to discover materials more quickly and inexpensively than was formerly possible. In some embodiments, search programs are employed to compare regions of TGase 1 and involucrin proteins involved in cross-linking and esterification to other proteins (e.g., mutants and other proteins involved in CE assembly) so that new derivative molecules that perform these functions can be more efficiently designed. In other embodiments, search programs are employed to compare regions of adaptors that interact with TGase 1 and, thereby modulate cross-linking or esterification or both, with other molecules such as peptides, peptidomimetics, and chemicals, so that new enzymes, adaptors, intermediates, ceramide reactants, and products can be predicted and manufactured. (Schneider, *Genetic Engineering News* December: page 20 (1998), Tempczyk et al., *Molecular Simulations Inc. Solutions* April (1997), and Butenhof, *Molecular Simulations Inc. Case Notes* (August 1998)). This process of directed combinatorial chemistry is referred to as "rational molecule design". Thus, one goal of the rational molecule design of the invention is to produce structural analogs of biologically active polypeptides of interest (e.g., TGase 1 or involucrin) or of small molecules with which they interact in order to fashion molecules that are, for example, more or less potent forms of the polypeptide of interest. (See, e.g., Hodgson, *Bio. Technology* 9:19–21 (1991)). Rational molecule design has been used to develop HIV protease inhibitors and agonists for five different somatostatin receptor subtypes. (Erickson et al., *Science* 249:527–533 (1990) and Berk et al., *Science* 282:737 (1998)). Libraries of molecules that resemble TGase 1 and involucrin proteins can be created, incorporated into carrier systems, screened in the assays described herein, and profiles for these molecules can be constructed.

By starting with the sequence or protein models TGase 1 and involucrin proteins or fragments thereof, polypeptides having two-dimensional and/or three-dimensional homology can be rapidly identified. In a two-dimensional approach, a percent sequence identity can be determined by standard methods that are commonly used to compare the similarity and position of the amino acid of two polypeptides. Using a computer program such as BLAST or FASTA, two polypeptides are aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{total number of identical matches}}{[\text{length of the longer sequence within the matched span} + \text{number of gaps introduced into the longer sequence in order to align the two sequences}]} \times 100$$

Accordingly, the protein sequence corresponding to TGase 1 and involucrin proteins or fragments thereof is compared to known sequences on a protein basis. Protein sequences corresponding to TGase 1 and involucrin proteins or fragments thereof are compared, for example, to known amino acid sequences found in Swissprot release 35, PIR release 53 and Genpept release 108 public databases using BLASTP with the parameter W=8 and allowing a maximum of 10 matches. In addition, the protein sequences encoding TGase 1 and involucrin proteins or fragments thereof are compared to publicly known amino acid sequences of Swissprot using BLASTX with the parameter E=0.001. The candidate polypeptides can have the following degrees of homology to TGase 1 or involucrin proteins or fragments thereof, for example: 50%, 51%, 52%, 53%, 54%, 55%, 56%, 57%, 58%, 59%, 60%, 61% 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. The candidate polypeptides having greater than or equal to 50% homology are identified and are subsequently examined using the functional assays described herein. Candidate polypeptides that can be incorporated into carrier systems are, thus, identified and can be analyzed using the assays above so as to generate profiles of the molecules and compositions.

Additionally, a search program is used to compare the three-dimensional structure of TGase 1 and involucrin proteins or fragments thereof with other known three-dimensional structures so as to identify other enzymes and adaptors. In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221–239 (1971). Using this technique, it is possible to elucidate three-dimensional structure with good precision. Additionally, protein structure may be determined through the use of techniques of neutron diffraction, or by nuclear magnetic resonance (NMR). (See, e.g., Moore, W. J., Physical Chemistry, 4$^{th}$ Edition, Prentice-Hall, N.J. (1972)).

Alternatively, the protein model embodiments are constructed using computer-based protein modeling techniques. By one approach, the protein folding problem is solved by finding target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of a polypeptide of interest. (See e.g., Srinivasan, et al., U.S. Pat. No. 5,557,535 issued Sep. 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using the distance geometry program DRAGON which constructs a low resolution model. A full-atom representation is then constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., Proteins:Structure, Function, and Genetics, Supplement 1:38–42 (1997)).

In one approach, a three-dimensional structure of a polypeptide of interest (e.g., TGase 1 or involucrin proteins or fragments thereof) is determined by x-ray crystallography, NMR, or neutron diffraction and computer modeling, as described above. Useful protein models of the polypeptide of interest can also be gained by computer modeling alone. Combinatorial chemistry is then employed to design derivatives of the polypeptide of interest based on the three-dimensional models. The candidate proteins are then tested in the functional assays decribed herein. The assays, described herein and assays that evaluate the effectivity of a carrier system, as will be apparent to one of skill in the art given the disclosure herein, (referred to collectively as "carrier system characterization assays") are performed on the newly identified proteins and based on the performance in the carrier system characterization assays, the results are recorded on a computer readable media and a profile is created. Further cycles of modeling and carrier system characterization assays are employed to more narrowly define the parameters needed in an enzyme or adaptor that elicits a desired response.

For example, a novel enzyme or adaptor can be identified as follows. First, a molecular model of TGase 1 or involucrin proteins or fragments thereof are created using one of the techniques discussed above or as known in the art. Next, chemical and peptide libraries and protein sequence databases are searched for molecules similar in structure to the polypeptide of interest. Identified candidate molecules are then screened in the carrier system characterization assays, described above, and the agents that produce the desired profiles are used as templates for further library construction. Libraries of related polypeptides are synthesized and these molecules are then used in the carrier system characterization assays. Compounds that produce desirable responses are identified, recorded on a computer readable media, (e.g., a profile is made) and the process is repeated to select for optimal enzymes and adaptors.

Each newly identified enzyme and/or adaptor and its performance in the carrier system characterization assay is recorded on a computer readable media and a database or library of profiles are generated. These profiles are used by researchers to identify important property differences between active and inactive molecules so that compound libraries are enriched for molecules that have favorable characteristics.

In another embodiment, computer modeling and the sequence-to-structure-to-function paradigm is exploited to identify novel enzymes and adaptors. By this approach, first the structure of TGase 1 or involucrin proteins or fragments thereof having a known response in a carrier system characterization assay is determined from its sequence using a threading algorithm, which aligns the sequence to the best matching structure in a structural database. Next, the protein's active site (i.e., the site important for a desired response in the carrier system characterization assay) is identified and a "fuzzy functional form" (FFF)—a three-dimensional descriptor of the active site of a protein—is created. (See e.g., Fetrow et al., *J. Mol. Biol.* 282:703–711 (1998) and Fetrow and Skolnick, *J. Mol. Biol.* 281: 949–968 (1998)).

The FFFs are built by itteratively superimposing the protein geometries from a series of functionally related proteins with known structures. The FFFs are not overly specific, however, and the degree to which the descriptors can be relaxed is explored. In essence, conserved and functionally important residues for a desired response are identified and a set of geometric and conformational constraints for a specific function are defined in the form of a computer algorithm. The program then searches experimentally determined protein structures from a protein structural database for sets of residues that satisfy the specified constraints. In this manner, homologous three-dimensional structures can be compared and degrees (e.g., percentages of three-dimensional homology) can be ascertained.

By using this computational protocol, genome sequence data bases such as maintained by various organizations including: tigr.org/tdb. genetics.wisc.edu, stanford.edu/~ball, hiv-web.lanl.gov, ncbi.nlm.nih.gov, ebi.ac.uk, patteur.fr/other/biology, and genome.wi.mit.edu, can be rapidly screened for specific protein active sites and for identification of the residues at those active sites that resemble a desired molecule. Several other groups have developed databases of short sequence patterns or motifs designed to identify a given function or activity of a protein. These databases, notably Prosite (expasy.hcuge.ch/sprot/prosite), Blocks (blocks.fhcrc.ora), and Prints (biochem.ucl.ac.uk/bsm/dbfrowser/PRINTS/PRINTS), use short stretches of sequence information to identify sequence patterns that are specific for a given function; thus they avoid the problems arising from the necessity of matching entire sequences. In this manner, new enzymes and adaptors are rationally selected for further identification by carrier system characterization assays, as described above. Rounds or cycles of functional assays on the molecules and derivatives thereof and further FFF refinement and database searching can be done.

Many computer programs and databases can be used with embodiments of the invention to identify novel enzymes and adaptors. The following list is intended not to limit the invention but to provide guidance to programs and databases which are useful with the approaches discussed above. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA*, 85: 2444 (1988)), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell *J.* Mol. Biol. 234:217–241 (1997)), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the teachings herein.

The section below describes the manufacture of several proteins (e.g., mutant TGase 1, mutant involucrin, and delivery agents) that can be used to construct carrier systems.

Mutant TGase 1 and Involucrin and Protein Expression

Mutant TGase 1, mutant involucrin, and mutant forms of other enzymes and adaptors can be used in several embodiments. In some cases, mutations in these proteins have little or no structural or functional effect and are therefore considered equivalents of TGase 1 or involucrin. That is, functionally equivalent amino acid residues can be substituted for residues within the protein's sequence resulting in a silent change. Accordingly, one or more amino acid residues within the TGase 1 and involucrin proteins or fragments thereof can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

Additionally, mutations of TGase 1 and involucrin and other enzymes and adaptors can be created so as to effect a structural or functional changes or both. These mutant proteins can be analyzed in the carrier system characterization assays and profiles of the molecules can be generated. These mutant protein profiles can then be compared to wild-type protein profiles so as to determine if the mutation resulted in a gain or loss of function. In this manner, mutations that produce desired functional responses can be selected for and optimal molecules can be created. Mutations that result in a silent change and ones that result in a gain or loss of function can be created by using site-directed mutagenesis and other techniques known to those of skill in the art. Additionally, TGase 1, involucrin, and other enzymes and adaptors can be created so that the protein is differentially modified during or after translation, e.g., by phosphorylation, glycosylation, cross-linking, acylation, or proteolytic cleavage. (Ferguson et al., Ann. Rev. Biochem. 57:285–320 (1988)).

To express many of the enzymes, adaptors, and delivery agents, nucleic acids containing the coding sequence for protein are obtained and cloned into a suitable expression vector such that the coding region is operably linked to a heterologous promoter. The nucleic acid encoding the protein or polypeptide to be expressed is operably linked to a promoter in an expression vector using conventional cloning technology. The expression vector can be in any of the mammalian, yeast, amphibian, insect, parasite, or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism in which the expression vector is introduced, as explained by Hatfield, et al., U.S. Pat. No. 5,082,767, incorporated herein by this reference. Further, a secretory leader sequence can be incorporated so as to facilitate purification of the protein.

The following is provided as one exemplary method to express the proteins encoded by the nucleic acids described above. First, the methionine initiation codon for the gene and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the nucleic acid lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). The vector pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding the polypeptide to be expressed can be obtained by PCR from the bacterial vector using oligonucleotide primers complementaiy to the nucleic acid and containing restriction endonuclease sequences for PstI incorporated into the 5 prime primer and BglII at the 5 prime end of the corresponding cDNA 3 prime primer, taking care to ensure that the nucleic acid is positioned in frame with the poly A signal. The purified fragment obtained from the resulting PCR reaction is digested with PstI, blunt ended with an exonuclease, digested with BglII, purified and ligated to pXT1, now containing a poly A signal and digested with BglII. The ligated product is transfected into a suitable cell line, e.g., mouse NIH 3T3 cells, using Lipofectin (Life Technologies, Inc., Grand Island, N.Y.) under conditions outlined in the product specification. Positive transfectants are selected after growing the transfected cells in 600 ug/ml G418 (Sigma, St. Louis, Mis.). Preferably the expressed protein is released into the culture medium, thereby facilitating purification.

Alternatively, nucleic acids encoding the polypeptide of interest can be cloned into pED6dpc2 and the resulting pED6dpc2 constructs can be transfected into a host cell, such as COS 1 cells. Methotrexate resistant cells are selected and expanded. Preferably, the protein expressed is released into the culture medium thereby facilitating purification.

Another embodiment utilizes the "Xpress system for expression and purification" (Invitrogen, San Diego, Calif.). The Xpress system is designed for high-level production and purification of recombinant proteins from bacterial, mammalian, and insect cells. The Xpress vectors produce recombinant proteins fused to a short N-terminal leader peptide which has a high affinity for divalent cations. Using a nickel-chelating resin (Invitrogen), the recombinant protein can be purified in one step and the leader can be subsequently removed by cleavage with enterokinase.

One preferred expression vector is the pBlueBacHis2 Xpress. The pBlueBacHis2 Xpress vector is a Baculovirus expression vector containing a multiple cloning site, an ampicillin resistance gene, and a lac z gene. By one approach, the nucleic acid encoding the polypeptide of interest is cloned into the pBlueBacHis2 Xpress vector and SF9 cells are infected. The expression protein is then isolated or purified according to the maufacturer's instructions.

Proteins in the culture medium can also be separated by gel electrophoresis. The separated proteins are then detected using techniques such as Coomassie or silver staining or by using antibodies against the protein. Coomassie, silver staining, and immunolabeling of proteins are techniques familiar to those skilled in the art. If desired, the proteins can also be ammonium sulfate precipitated or separated based on size or charge prior to electrophoresis.

The polypeptide of interest can also be purified using standard immunochromatography techniques. In such procedures, a solution containing the protein, such as the culture medium or a cell extract, is applied to a column having antibodies against the protein attached to the chromatography matrix. The protein is allowed to bind the immunochromatography column. Thereafter, the column is washed to remove non-specifically bound proteins. The specifically bound protein is then released from the column and recovered using standard techniques.

The term "isolated" requires that the material be removed from its original environment (e.g., the natural environment if it is naturally occurring). For example, a naturally occurring nucleic acid or protein present in a living cell is not isolated, but the same nucleic acid or protein, separated from some or all of the coexisting materials in the natural system, is isolated. In accordance with this definition, polypeptide of interest present in a cell lysate is "isolated". The term "purified" does not require absolute purity; rather it is intended as a relative definition. For example, recombinant nucleic acids and proteins are routinely purified to electrophoretic homogeneity, as detected by ethidum bromide staining or Coomassie staining, and are suitable in several assays despite having the presence of contaminants.

In addition to isolating or purifying polypeptides of interest by using recombinant DNA techniques, these molecules can be prepared by chemical synthesis methods (such as solid phase peptide synthesis) using methods known in the art such as those set forth by Merrifield et al., J. Am. Chem. Soc. 85:2149 (1964), Houghten et al., Proc. Natl. Acad. Sci. USA, 82:51:32 (1985), and Stewart and Young (solid phase peptide synthesis, Pierce Chem Co., Rockford, Ill. (1984). Such polypeptides can be synthesized with or without a methionine on the amino terminus. Chemically synthesized polypeptides can be oxidized using methods set forth in these references to form disulfide bridges.

In several embodiments, enzymes, adaptors, delivery agents, and ceramide reactants are joined to a support to facilitate the study of CE assembly (e.g., to isolate proteins involved in assembly of the CE), to test the efficacy of therapeutic agents, and to provide a carrier system that can deliver an active ingredient or delivery agent. The next section describes the preparation of several supports for use with some embodiments.

Preparation of Multimeric Supports and Multimerized Enzymes, Adaptors, and Delivery Agents While a natural monomeric agent (that is, an agent that presents a discrete molecule, thus, carrying only one binding epitope or domain) is oftentimes of sufficient affinity to achieve its intended purpose, a synthetic agent or a multimeric agent (that is, an agent that presents multiple molecules, thus, having several binding epitopes or domains) often times has greater ability to achieve this purpose. It should be noted that the term "multimeric" refers to the presence of more than one molecule on an agent, for example, several individual molecules of an antibody joined to a support, as distinguished from the term "multimerized" which refers to an agent that has more than one molecule joined as a single discrete compound molecule on a support, for example several antibody molecules joined to form a single compound molecule that is joined to a support.

A multimeric agent (synthetic or natural) can be obtained by joining to a macromolecular support a plurality of enzymes, a plurality of enzymes joined to a plurality of adaptors, and a plurality of enzymes joined to a plurality of adaptors, wherein the adaptors are also joined to a plurality of delivery agents. Additionally, multimeric agents can be obtained by joining the compositions described above to a plurality of ceramide reactants. A "support" is also termed a carrier, a resin or any macromolecular structure used to join or immobilize a molecule. Solid supports include, but are not limited to, the walls of wells of a reaction tray, test tubes, polystyrene beads, magnetic beads, nitrocellulose strips, membranes, microparticles such as latex particles, sheep (or other animal) red blood cells, Duracyte® artificial cells, SLVs and others.

In several emodiments, the macromolecular support has a hydrophobic surface that interacts with a portion of the protein(s) of interest by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, enzymes, adaptors, intermediates, and products can be covalently bound to carriers including proteins and oligo/polysaccharides (e.g. cellulose, starch, glycogen, chitosane or aminated sepharose). In these later embodiments, reactive groups on the proteins, such as a hydroxy or an amino group, are used to join to a reactive group on the carrier so as to create the covalent bond. Embodiments also comprise a support with a charged surface that interacts with the enzymes, adaptors, intermediates, and products. Additional embodiments comprise a support that has other reactive groups that are chemically activated so as to attach enzymes, adaptors, intermediates, and products. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma). Inorganic carriers, such as silicon oxide material (e.g. silica gel, zeolite, diatomaceous earth or aminated glass) to which the enzymes, adaptors, intermediates, and products are covalently linked through a hydroxy, carboxy or amino group and a reactive group on the carrier are also embodiments.

In another embodiment, linkers, such as 8 linkers (flexible regions of 8 phage), of an appropriate length are inserted between one or more of the molecules that are joined to the support (e.g., linkers are placed between adaptors and delivery agents) so as to encourage greater flexibility and thereby overcome any steric hindrance that is presented by the support or molecules thereon. The determination of an optimal length of linker is made by screening the carrier system having varying linkers in the carrier system characterization assays decribed in the herein.

A composite support comprising more than one type of enzyme, adaptor, delivery agent, and ceramide reactant is also an embodiment. A "composite support" is a carrier, a resin, or any macromolecular structure used to join or immobilize two or more different enzymes, adaptors, delivery agents, or ceramide reactants. Linkers, such as 8 linkers, can also be found on the composite supports of the invention.

In other embodiments, the multimeric and composite supports discussed above have attached multimerized proteins. A multimerized protein is obtained by, for example, creating an expression construct having two or more nucleotide sequences encoding the polypeptide of interest joined together. The expressed multimerized protein can then be joined to a support. A support having many such multimerized agents is termed a multimerized-multimeric support. The multimerized form of a protein can be advantageous for many applications because of the ability to obtain an agent with greater functional properties. The incorporation of linkers or spacers, such as flexible 8 linkers, between the protein domains that make-up the multimerized agent can also be advantageous for some embodiments. The next section describes several embodiments that have therapeutic and/or prophylactic and/or cosmetic application.

Pharmaceutical Embodiments

Many embodiments are suitable for treatment of subjects either as a preventive measure to avoid skin disorders, such as ichthyosis-related maladies, or as a therapeutic to treat subjects already afflicted with a skin disorder. Although anyone could be treated with these agents as a prophylactic, the most suitable subjects are people at risk for such diseases. Such subjects include, but are not limited to, individuals with a family history of ichthyosis-related diseases.

The carrier systems described herein can be processed in accordance with conventional pharmacological and cosmetological methods to produce medicinal agents and cosmetics for administration to patients, e.g., mammals including humans. The carrier systems, for example, can be incorporated into a pharmaceutical or cosmetic product with and without modification. The compositions can be employed in admixture with conventional excipients, i.e., pharmaceutically acceptable organic or inorganic carrier substances suitable for topical application that do not deleteriously react with the molecules that assemble the carrier system. Suitable acceptable carriers can be water, salt solutions, alcohols, oils, glycols, gelatine, carbohydrates such as lactose, amylose or starch, fatty acid monoglycerides and diglycerides, pentaerythritol fatty acid esters, hydroxy methylcellulose, polyvinyl pyrrolidone, etc. The preparations can be sterilized and if desired mixed with auxiliary agents, e.g., lubricants, preservatives, stabilizers, wetting agents, emulsifiers, salts for influencing osmotic pressure, buffers, coloring, aromatic substances and the like that do not deleteriously react with the active compounds. They can also be combined where desired with other active agents.

The effective dose and method of administration of a carrier system formulation can vary based on the individual patient and the stage of the disease, as well as other factors known to those of skill in the art. Therapeutic efficacy and toxicity of such compounds can be determined by standard pharmaceutical or cosmetological procedures with experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical and cosmetological compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Short acting compositions are administered daily whereas long acting pharmaceutical compositions are administered every 2, 3 to 4 days, every week, or once every two weeks. Depending on half-life and clearance rate of the particular formulation, the pharmaceutical compositions are administered once, twice, three, four, five, six, seven, eight, nine, ten or more times per day.

The concentrations of the carrier systems in a specific formulation can be quite high in some embodiments. Desirable concentrations for topical administration, for example, range from 10:M to 2M. Preferable concentrations for these embodiments range from 100:M to 500 mM. For example, preferred concentrations for use in topical applications include 100:M, 110:M, 120:M, 130:M, 140:M, 145:M, 150:M, 160:M, 170:M, 180:M, 190:M, 200:M, 220:M, 240:M, 250:M, 260:M, 280:M, 300:M, 320:M, 340:M, 360:M, 380:M, 400:M, 420:M, 440:M, 460:M, 480:M, 500:M, 550:M, 600:M, 650:M, 700:M, 750:M, 800:M, 850:M, 900:M, 1 mM, 5 mM, 10 mM, 15 mM, 20 mM, 25 mM, 30 mM, 35 mM, 40 mM, 45 mM, 50 mM, 60 mM, 70 mM, 80 mM, 90 mM, 100 mM, 120 mM, 130 mM, 140 mM, 150 mM, 160 mM, 170 mM, 180 mM, 190 mM, 200 mM, 300 mM, 325 mM, 350 mM, 375 mM, 400 mM, 425 mM, 450 mM, 475 mM, and 500 mM. More specifically, the dosage of the therapeutic, prophylactic, and cosmetic is one that provides sufficient carrier system to attain a desirable effect including formation of the CE.

Routes of administration of the carrier system are primarily topical, although it is desired to administer some embodiments to cells that reside in deep skin layers. Topical administration is accomplished via a topically applied cream, gel, rinse, etc. containing the carrier system. Compositions of carrier system-containing compounds suitable for topical application include, but not limited to, physiologically acceptable implants, ointments, creams, rinses, and gels. Any liquid, gel, or solid, pharmaceutically acceptable base in which the carrier systems are at least minimally soluble is suitable for topical use. The example below describes an approach that can be used to test embodiments for the ability to treat icthyosiform-related diseases.

EXAMPLE 1

Evaluating the Efficacy and Dose of the Carrier Systems

The discussion below describes an approach to evaluate the efficacy and dose of a pharmaceutical and/or cosmetic embodiment. A mouse model for lamellar ichthyosis has been created and these mice can be used to evaluate the efficacy of the various compositions. (See e.g., Matzuki et al., Proc. Natl. Acad. Sci. USA 95: 1044–1049 (1998), herein expressly incorporated by reference in its entirety). Mice lacking the TGase 1 gene are obtainable through Matzuki et al., or can be obtained through commercial sources that specialize in manufacturing transgenic and "knock-out" mice to order.

Alternatively, these mice can be constructed by following the protocol detailed in Matzuki et al., Proc. Natl. Acad. Sci. USA 95: 1044–1049 (1998), herein expressly incorporated by reference in its entirety. Briefly, TGase 1 knock-out mice are achieved by targeted disruption of the TGase 1 gene, that is replacing exons 1–3 with a Neo cassette by using homologous recombination in R1 ES cells. These exons encode the translation initiation codon and an N-terminal stretch unique to TGase 1 that is required for membrane anchoring. ES cell clones are screened by polymerase chain reaction (PCR) and Southern blot analysis and mutant ES clones carrying the targeted allele are used to generate chimeric animals. Northern blot analysis of heterozygous and homozygous chimeric animals is performed to verify the level of TGase-1 expression.

Heterozygous individuals (TGase $1^{+/-}$) will have the same phenotype as wild-type mice, however, homozygous individuals (TGase $1^{-/-}$) will present skin that is erythematous and shiny resembling the appearance of a collodian baby. Further, TGase$^{-/-}$ individuals that are left untreated with the carrier systems described herein will die within 4–5 hours after birth. Because of the short life-span of homozygous individuals, carrier systems to be tested are prepared in advance, and preferred formulations are liquid or gel.

To screen the carrier systems, TGase $1^{-/-}$ mice are breed and shortly after birth, the mice are dipped into a formulation comprising carrier system. Over the course of several experiments, many concentrations of product (e.g., TGase 1, involucrin, and lipid Z joined to an SLV) can be analyzed but initial determinations are made with sufficient formulation of product to deliver a concentration of 1 mM of enzyme, adaptor, and ceramide reactant. In initial experiments, after administration of the carrier system, the time period of survival of treated mice, as compared to untreated mice, is determined. A greater period of survival of carrier system-treated TGase $1^{-/-}$ mice than untreated TGase $1^{-/-}$ will be observed.

Additionally, the transdermal water loss (TEWL) of treated TGase$^{-/-}$ mice is compared to that of untreated TGase $1^{-/-}$ mice. To assess TEWL, an evaporimeter is used to analyze the dorsal skin of the animals. The Courage and Khazaka Tewameter TM210, an open chamber system with two humidity and temperature sensors, can be used to measure the water evaporation gradient at the surface of the skin. The parameters for calibrating the instrument and use of the instrument is described in Barel and Clarys *Skin Pharmacol.* 8: 186–195 (1995), herein expressly incorporated by reference in its entirety and the manufacturer's instructions. In the controls, TEWL will be low in wild-type and heterozygous mice but will be approximately 100 fold greater in untreated homozygous mice. The TEWL reading on homozygous mice that were treated with a carrier system will approach the reading obtained from untreated wild-type or untreated heterozygous mice.

Further, skin barrier function will be analyzed by examining the percutaneous absorption of [$^3$H] mannitol across full thickness, excised skin. Treated and untreated mouse dorsal skins, as well as dorsal skins from untreated wild-type and homozygous controls, are excised and mounted in side-by-side diffussion chambers (effective surface area: 0.126 cm$^2$) and are allowed to stabilize at 37° C. with Ringer's solution (pH 7.4). Donor and receiver fluid volumes are 1.5 ml. After 1 hour of incubation, [$^3$H] mannitol (NEN) is added to the epidermal donor fluid to yield a final concentration of 10:Ci/ml. Five hundred:l of receiver fluid is removed at various time points, an equal volume of Ringer's is added to the system, and the radioactivity is determined by scintillation counting. In untreated TGase $1^{-/-}$ mice, the steady-state flux of radioactive mannitol in the skin will be greater than 1000 times that of treated TGase $1^{-/-}$ mice, untreated heterozygous mice, and untreated wild-type mice.

As another method of analysis, the diffusion of the fluorescent dye Lucifer yellow in the skin of carrier system-treated TGase 1$^{-/-}$ mice is compared to that of untreated TGase 1$^{-/-}$ mice, untreated heterozygous mice, and untreated wild-type mice. Accordingly, neonatal mice are restrained in a petri dish with their backs in contact with 1 mM Lucifer yellow in Ringer's solution (pH 7.4) at 37° C. After one hour, the mice are sacrificed, then frozen, and dorsoventrally sliced at a thickness of 5:m. The sections are counter stained with 5:g/ml propidium iodide and are analyzed by fluoresence microscopy. The dye will be retained in the upper layers of the stratum corneum in the untreated wild-type mice, untreated heterozygous mice, and the carrier-system treated TGase –/– mice but the untreated homozygous mice will be found to have the dye distributed throughout the stratum corneum and the dermal layers.

By applying the techniques described in this example, one of skill can readily evaluate the effectivity and dose of the carrier systems described herein for the treatment and prevention of lamellar ichthyosis. The example below provides some of the materials and methods used in the preceding experiments.

EXAMPLE 2

Production of Recombinant TGase 1 and 3 Enzymes

Recombinant full-length human TGase 1 and TGase 3 enzymes were expressed in Sf9 cells by the BaculoGold system using the pVL1392 plasmid vector (Pharmigen, San Diego, Calif.) as described previously (Candi, et al., *J. Biol. Chem.*, 273: 13693–13702 (1998), herein expressly incorporated by reference in its entirety). TGase 1 was recovered in the particulate fraction after sonication in lysis buffer. In some experiments this crude particulate fraction was used as the source of enzyme activity in amounts standardized to incorporate 0.7 pmol/min of $^{14}$C-putrescine into succinylated casein. In most experiments, it was solubilized from membranes by sonication in lysis buffer with 4% Triton X-100 or in some cases with 1 M NH$_2$OH—HCl. (Steinert, et al., *J. Biol. Chem.*, 271: 26242–26250 (1996), herein expressly incorporated by reference in its entirety). TGase 3 was recovered in the cytosolic fraction after lysis by sonication. These solutions were clarified by centrifugation and the enzymes subsequently purified by FPLC on MonoQ Sepharose. Active fractions were brought to 1 M Na$_2$SO$_4$ and rechromatographed on a 1 ml Resource Phe hydrophobic interaction column (Amersham Pharmacia Biotech, Piscataway, N.Y.) using a gradient from 1 M Na$_2$SO$_4$, 20 mM Tris-Cl (pH 8.0) to 20 mM Tris-Cl (pH 8.0) in 30 min at a 1 ml/min flow rate. The TGase 1 and 3 enzymes were >98% pure by SDS-PAGE, and could be stably stored as a suspension in 1.5 M Na$_2$SO$_4$ for some weeks at 4° C. Amounts were determined by amino acid analysis following acid hydrolysis. TGase 3 was activated with 0.1 U/100 µg of dispase for 15 min at 23° C. and purified from the protease on a MonoQ column as above.

Expression and Purification of Recombinant Human Involucrin

A full-length cDNA clone of human involucrin was obtained by PCR from human chromosomal DNA. PCR primers used were:

(+) GTAGCTTCTCATATGTCCCAGCAAC (SEQ.ID.NO. 11); and (–) CCCTTGTATGAGACGATCTGAG (SEQ. ID.NO. 12).

These were designed to create an NdeI restriction site to be compatible with the pET expression system (Novagen, Madison, Wis.). The PCR product was cloned into the pCR2.1 plasmid using the TA Cloning kit (Invitrogen, Carlsbad, Calif.) and verified by DNA sequencing. Following subcloning into the pET11a vector and transfection into the BL21(DE3)pLysS strain of *E. coli* (Novagen), protein expression was induced by 1 mM IPTG for 3 h. Cell mass was pelleted and lysed by freeze-thawing. Particulate matter was removed by centrifugation and involucrin protein was enriched by heat precipitation as described (Etoh, et al., *Biochem. Biophys. Res. Commun.*, 136: 51–56 (1986), herein expressly incorporated by reference in its entirety). It was purified to >97% (by SDS-PAGE) by anion exchange chromatography on a HiTrap Q column (Amersham Pharmacia Biotech) using 20 mM Tris-HCl (pH 8.0) and gradient elution with the same buffer containing 1 M NaCl. By circular dichroism, it possessed an estimated α-helix content of 68%. As this is similar to native involucrin isolated from keratinocytes (Yaffe, et al., *J. Biol. Chem.*, 267: 12233–12238 (1992), herein expressly incorporated by reference in its entirety), it is likely that the recombinant protein had assumed its native configuration.

Preparation of Synthetic Lipid Vesicles (SLV)

Mixtures of dipalmitoyl-phosphatidylcholine, cholesterol, dipalmitoyl-phosphatidylserine (PS) and other lipids where indicated (all from Sigma, St. Louis, Mo.) were made in chloroform-methanol (95:5). In all cases, the mixtures contained 30% cholesterol. When the amounts of PS or other individual components were varied, phosphatidylcholine was added to make the mixture to 100%. Mixtures were made in 0.5 ml and contained 10 µmol of total lipids. The solvent was flushed away under a stream of N$_2$, dried further under high vacuum for 4 h and then resuspended by vortexing in 0.5 ml of a buffer containing 50 mM Tris-Cl (pH 8.0), 100 mM NaCl, 3 mM NaN$_3$, 5 mM DTT, and 200 mM sucrose. The mixture was sonicated on ice five times each for 1 min using a Branson 250 sonifier with micro probe tip, and allowed to stand at 23° C. to facilitate assembly of SLV. After 1 h the SLV were diluted with 0.5 ml of the above buffer without sucrose, and 200 µl aliquots were centrifuged at 100,000× g for 30 min in a Beckman Airfuge using the A-10 rotor. The top 175 µl was removed, and the pellet resuspended in another 150 µl of sucrose-free buffer. The final stock concentration was 11 µmol/ml.

Assaying Membrane-Association of TGase 1, TGase 2, TGase 3, Involucrin, Loricrin, SPR1, SPR2 and Succinylated Casein Liver TGase 2 enzyme was obtained from Sigma. The recombinant human CE proteins loricrin (Candi, et al., *J. Biol. Chem.*, 270: 26382–26390 (1995), herein expressly incorporated by reference in its entirety), SPR1 (Candi, et al., *J. Biol. Chem.*, 274: 7226–7237 (1999), herein expressly incorporated by reference in its entirety) and SPR2 (Tarcsa, et al., *J. Biol. Chem.*, 273: 23297–23303 (1998), herein expressly incorporated by reference in its entirety) were expressed and purified as described previously. Succinylated casein was a generous gift of Dr. Soo-Youl Kim.

All binding essays were done at 23° C. in a final volume of 200 µl by mixing SLV with protein amounts empirically found to exceed at least two-fold the binding capacities of the SLV: for TGase 1, 20 µg (0.2 nmol) were mixed with 0.1 µmol of SLV lipids; for involucrin, 1.2 nmol were mixed with 1 µmol of SLV lipids; for all other proteins, 50 µg were used with 1 µmol of SLV lipids. In all cases, the buffer contained 50 mM Tris-HCl (pH 8.0), 100 mM NaCl, 1 mM DTT, 3 mM NaN$_3$, and other additives where noted. Some mixtures also contained 1 mM CaCl$_2$ or 2 mM EDTA. After mixing, the samples were centrifuged for 45 min at 100,000× g, and the protein content from 50 µl of supernatant was determined by amino acid analysis after acid hydrolysis. Data were usually not corrected for loss of SLV lipids, as in control experiments, cumulated losses were <4% as assayed by $^{14}$C-phosphatidylcholine tracer, and thus neglected from the calculations.

Preparation of Free $Ca^{++}$ Concentrations

The $Ca^{++}$ concentrations in the $\mu$M range were set by buffering free $Ca^{++}$ with chelators The desired $Ca^{++}$/chelator ratios were calculated by the WinMaxC 1.7 computer program (Bers, et al., *Methods in Cell Biology Vol 40: A Practical Guide to the Study of $Ca^{2+}$ in Living Cells*, Nuccitelli, R., ed., pp. 1–327 (1994), herein expressly incorporated by reference in its entirety), and were made by adding the required amounts of 1 M $CaCl_2$ to 0.2 M stock solutions of the following chelators at pH 8.0. Final chelator concentrations in the samples were 10 mM in all cases. Sodium citrate was the chelator for the 20–500 $\mu$M $Ca^{++}$ range; sodium nitrilotriacetate for the 1–20 $\mu$M $Ca^{++}$ range; and sodium 1,2-bis(aminophenoxy)ethane-N,N,N',N' tetraacetate for the 0.1–1 $\mu$M $Ca^{++}$ range. The actual concentration values were not significantly different from the theoretical calculations (p>0.2, n=5) in the 2–100 $\mu$M range as assayed by arsenazo III dye spectrophotometry (Thomas, M. V., *Cellular Calcium*, McCormack, et al., eds., pp. 115–123 (1991), herein expressly incorporated by reference in its entirety).

Identification of $^{14}$C-Putrescine-Labeled Involucrin Fragments and Measurement of the Reaction Rate Three sets of experiments were performed to determine reactive Gln residues in involucrin by TGase 1 and labeling with $^{14}$C-putrescine: TGase 1 bound to SLV (2 $\mu$mol of lipid) containing 15% PS; the TGase 1 enzyme present in crude Sf9 cell particulate fractions; or solubilized TGase 1 in reaction buffer. In each case, the amount of TGase 1 activity was standardized to 0.7 pmol/min using succinylated casein and $^{14}$C-putrescine, as described previously (Kim, et al., *J. Biol. Chem.*, 269: 27979–27986 (1994), herein expressly incorporated by reference in its entirety), and corresponded to about 0.9 pmol. This was set far below saturating amounts on SLV in order to ensure that all enzyme was bound to the SLV. All reactions were done in 250 $\mu$l and contained 1.2 nmol of involucrin, 1 mM $CaCl_2$, 20 mM putrescine with 100 nCi of $^{14}$C-putrescine (Dupont-New England Nuclear, Boston, Mass., 110 Ci/mmol).

After 4 h incubation at 37° C., the reactions were stopped by addition of EDTA to 10 mM and 100 $\mu$l 20% SDS, and vortexed. This mixture was precipitated and washed three times with acetone-triethylamine-acetic acid (90:5:5) (Konigsberg, W. H. and L. Henderson, *Meth. Enzymol.*, 91: 254–559 (1983), herein expressly incorporated by reference in its entirety) to remove the SDS and the lipids. After repeated washings with acetone, the pellet was redissolved in a buffer of 50 mM Tris-Cl (pH 7.5), and digested for 16 h at 37° C. with 2% (by weight) of modified trypsin (Boehringer Mannheim, Indianapolis, Ind.). Aliquots of 20 $\mu$g were resolved on a 250×4.6 mm Beckman Ultrasphere C18 HPLC column. Separated peaks were analyzed for radioactivity and peaks containing activity were attached to a solid support for sequencing as before (Steinert, P. M. and L. N. Marekov, *J. Biol. Chem.*, 270: 17702–17711 (1995), herein expressly incorporated by reference in its entirety). As the peptide number 40 eluted by 50% acetonitrile (see FIG. 9) was too long for direct sequencing, it was subjected to limited proteolysis by dispase and was sequenced from four peptides isolated by HPLC chromatography as above.

The Gln residues reacted by putrescine by TGase 1 were identified by standard protein sequencing analyses. The PTH-derivative of the $\lambda$-glutamylputrescine eluted as a novel peak at 13.55 min in the HPLC separation step of the Porton LF 3000 protein sequencer. This was confirmed by measurement of the $^{14}$C-putrescine label. This always corresponded to those cycles where a Gln residue was also present.

Determination of Kinetic Parameters of Putrescine Incorporation by TGase 1

Values were measured at 37° C. using 0.9 pmol TGase 1, 20 mM putrescine with 100 nCi of $^{14}$C-putrescine, 5 mM $CaCl_2$, SLV containing a total of 2 $\mu$mol total lipid, five concentrations of substrate proteins (0.2, 0.5, 1, 2 and 5 $\mu$M for SLV-bound TGase 1 with involucrin, or 5, 10, 20, 50 and 100 $\mu$M for solubilized TGase 1 and soluble substrates) as described (Candi, et al., *J. Biol. Chem.*, 270: 26382–26390 (1995), herein expressly incorporated by reference in its entirety). The calculated $K_M$ values pertain to the protein substrates; $V_{max}$ and $K_{cat}$ data are those for putrescine incorporation. The molar mass of succinylated casein was taken to be 25 kDa. The reaction rates were quantified by measuring the incorporated radioactivity as before (Thomas, M. V., *Cellular Calcium*, McCormack, et al., eds., pp. 115–123 (1991), herein expressly incorporated by reference in its entirety). Kinetic constants were obtained using the curve-fitting and regression analysis Sigmaplot 4.0 software. All data points represent the means of three measurements, each performed in triplicate. The size of SLV (>85% below 100 nm, as determined by size-exclusion on Sepharose CL-4B chromatography) was not significantly altered during the binding and labeling reactions.

Synthesis of N-[16-(16-hydroxyhexadecyl) oxypalmitoyl]-sphingosine (Lipid Z)

Lipid Z was synthesized starting from 16-hydroxy-hexadecanoic acid, 1,16 hexadecanediol and D-sphingosine by the following method. Five g (18 mmol) of 16-hydroxy-hexadecanoic acid (Aldrich) was added to a mixture of 0.75 ml 85% phosphoric acid, 2.525 g 100% phosphoric acid and 6.1 g KI in a pressure tube, sealed and incubated overnight at 120° C. The reaction mixture was taken up in chloroform, washed with 0.1 M sodium thiosulfate, 0.1 N HCl, water and tried with $Na_2SO_4$. After the evaporation of the solvent, the resulting oil was taken up in 15 ml chloroform-methanol 95.5 and chromatographed on 150 g Kieselgel 60 (Merck) by washing with 250 ml and eluting with 300 ml the same solvent. After evaporation of the solvent, 2.1 g of 16-iodo-hexadecanoic acid was obtained (31%).

1 g of 1,16-hexadecanediol (Aldrich) 3.9 mmol) was fully converted to its sodium di-alcholoate by adding 200 mg NaH to it in 20 ml dry tetrahydrofurane.

1.48 g (3.9 mmol) 16-iodo-hexadecanoic acid was added to this stirred slurry under argon and refluxed for 6 h. The solvent was evaporated and the product was dissolved in a warm mixture of chloroform and 1 N HCl, washed with water until neutral and dried with $Na_2SO_4$. This mixture of the initial organic reagents, 16,16'-[1,16-hexadecanediylbis (oxy)]bis[hexadecanoic acid] and the product 16-(16-hydroxyhexadecanoly)oxyhexadecanoic acid was separated by chromatography on 100 g Kieselgel 60 in chloroform-methanol 95:5 ($R_f$-0.4). After evaporation of the solvent, 540 mg 16(16-hydroxy-hexadecanoxy-hexadecanoic acid was obtained (55%), which was then acetylated, coupled to sphingosine base (Calbiochem) and saponified as described (Hammarstroem, S., (1971) *J. Lipid Res.* 12, 760–765), herein expressly incorporated by reference in its entirety. The resulting N-[16-(16-hydroxyhexadecyl)oxypalmitoyl]-sphyngosine (yield:61%) was purified by preparative Kieselgel 60 TLC developed with chloroform:acetone:methanol:acetic acid:water 10:4:3:2:1 (Rf: 0.65).

Chemical Analysis

16-Iodohexadecanoic acid:

M. P.: 87–88° C. (from pet. ether)

$^1$H-n.m.r.: (Bruker 250 MHz, CDCl$_3$) δ 1.2–1.40 and 1.45–1.7 (m, 24H+6H, —CH$_2$O 2.4 (t, 2H, 8 Hz, —CH$_2$.CO—), 3.17 (t, 2H, J=7 Hz, —CH$_2$—I)

Mass spect. (FAB, mb): M+H$^+$=383.3 m/z

Anal. Calc. for C$_{16}$H$_{31}$IO$_2$ (382.32): C, 50.27; H, 8.17; I, 33.19; Found C, 50.29; H, 8.12; I, 33.4.

16-(16-hydroxyhexadecyl)oxyhexadecanoic Acid:

M. P.: 91° C. (from pet. ether)

$^1$H-n.m.r.: (250 MHz, CDCl$_3$) δ 1.2–1.4 and 1.45–1.7 (m, 44+10H, —CH$_2$—), 2.25 (t,2H, J 7.8 Hz, —COCH$_2$—), 3.34 (t, 4H, J 6.9 Hz, —CH$_2$—O—CH$_2$—), 3.56 (t, 2H, J 7 Hz, —CH$_2$—OH)

Mass spect. (FAB, mb): M+H$^+$=513.8 m/z

Anal. Calc. for C$_{32}$H$_{64}$O$_4$ (512.85): C, 0.75; H, 12.5. Found C, 74.75; H, 12.45.

N-[16-(16-hydroxyhexadecyl)-oxyhexandecanoyl]-D-sphingosine:

M. P.: 96–97° C. (from pet. ether)

$^1$H-n.m.r.: (250 MHz, CDCl$_3$) δ 0.88 (t, 3H, Me), 1.0–1.4 and 1.45–1.7 (m, 68H+12H, —CH$_2$—), 2.05 (~q, 2H, J$_{5,6}$=J$_{6,7}$=~yHz, —CH=CH—CH$_2$—), 2.24 (t, 2H, J 7.8 Hz, —COCH$_2$—), 3.34 (t, 4H, J 6.9 hz, —CH$_2$—O—CH$_2$—), 3.5–3.7 (m, 5H, H-1 and CH$_2$OH), 3.75–3.9 (m, 2H, H-1',2), 4.3 (~t, 1H, J$_{2,2}$~5, J$_{3,4}$ 6.6 Hz, H-3), 5.55(~dd, 1H, J$_{4,5}$ 15.5 Hz, H-4), 5.84 (1H, J5,6(6~yHz, H-5).

I.R.: (Perkin Elmer IR 1600, KBr) v 3600–3100 (OH, NH), 1650 and 1550 (amide), and 1240 cm$^{-1}$ (ether)

High Resolution FAB Mass Spectrometry:

794.3464 m/z (calcd for C$_{50}$H$_{99}$NO$_5$: 794.3459)

Anal. Calc. for C$_{50}$H$_{99}$NO$_5$: C, 75.60H, 12.56; N, 1.76. Found C, 75.37; H, 12.51; N, 1.74.

Preparation of SLV Having Lipid Z

A mixture of 54 mol % dimyristoyl-phosphatidylcholine, 15 mol % dipalmitoyl-phosphatidylserine, 30 mol % cholesterol (all from Sigma, St. Louis, Mo.) and 1 mol % lipid Z was made in chloroform: methanol (9:1). This solution was dried down, taken up in aqueous buffer and dispersed by sonication as before (Nemes et al., *J. Biol. Chem.*, 274: in press (1999)). The SLV suspension was equipped with TGase 1 enzyme by incubation at 37° C. for 15 min prior to adding substrates. The amount of TGase 1 used was standardized to an activity level of 0.7 pmol/min using succinylated casein and 14C putrescine as substrates as described (Candi et al., *Proc. Natl. Acad. Sci. USA*, 95: 2067–2072 (1998), herein expressly incorporated by reference in its entirety).

Reactions of TGase 1 with Involucrin and Lipid Z

SLV (2 μmol lipid) were brought to 37° C. and 1 mM CaCl$_2$, and 0.6 nmol (40 μg) involucrin was added to make a total volume 200 μl, and incubated for 60 min, if not otherwise stated. The reactions were stopped by the addition of EDTA to 10 mM. Some reaction mixtures contained 1 mM putrescine, or alternatively, putrescine to 20 mM was added after running the reaction for 45 min.

Isolation of Lipid-Attached Involucrin Fragments

Following reaction, 0.1 ml 20% SDS in water was added to the samples and the mixture was vortexed. This mixture was precipitated and washed three times with acetone-triethylamine-acetic acid (90:5:5) to remove the SDS and the unbound lipids (Konigsberg, W. H. and L. Henderson, *Meth. Enzymol.*, 91: 254–259 (1983), herein expressly incorporated by reference in its entirety). After further washing with acetone the pellet was dried under vacuum and redissolved in 50 mM Tris-HCl (pH 7.5). Resolubilized protein was digested for 16 h with 2 mol % modified trypsin (Boehringer Mannheim). Peptides were resolved on a 250×2 mm PrimesphereC4 HPLC column (Phenomenex) and separated using a gradient elution from 75% buffer A (0.1% TFA in water) to 75% buffer B (50% 2-propanol in acetonitrile) in 40 min. Under these conditions, lipo-peptides were retarded but free peptides elute with the solvent front (Marekov, L. N. and P. M. Steinert, *J. Biol. Chem.*, 273: 17763–17770 (1998), herein expressly incorporated by reference in its entirety).

Protein Chemistry Procedures

Amino acid analysis of hydrolyzed samples (5.7 N HCl at 110° C. for 24 h in vacuo) was used to routinely measure amounts of lipo-peptides. Aliquots of isolated lipo-peptide peaks were attached to a solid support for sequencing (Marekov, L. N. and P. M. Steinert, *J. Biol. Chem.*, 273: 17763–17770 (1998), herein expressly incorporated by reference in its entirety). Saponification of lipo-peptides was done with 1 N KOH in 80% methanol for 2 h at 37° C., after which the solution was acidified, dried and peptides were recovered by HPLC on a C18 column. The availability of the free hydroxyl groups in positions 1 and 3 on the sphingosine moieties in the lipo-peptides was demonstrated by reacting ~1 nmol of lyophilized lipo-peptides in 100 μl in CHCl3: dimethyl acetonide (4:1) in the presence of a trace of camphersulfonic acid for 1 h at 37° C., followed by saponification with 1 N KOH and extraction of the lipids with chloroform: methanol (95:5).

Mass Spectrometry

Mass analysis was done either using Fast Atom Bombardment (positive ion mode, magic bullet) or electrospray ionization mass spectrometry for peptides. Spectra were acquired on a JEOL SX102 mass spectrometer fitted with an Analytica electrospray source.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A composition comprising transglutaminase (TGase) I and a synthetic lipid vesicle, wherein said synthetic lipid vesicle comprises a synthetic omega-hydroxyceramide.

2. The composition of claim 1, wherein said TGase I is recombinant.

3. The composition of claim 1, wherein said synthetic lipid vesicle comprises phosphatidylserine, phosphatidyicholine, or cholesterol, or mixtures thereof.

4. The composition of claim 1, wherein said synthetic omega-hydroxyceramide is 16-(16-hydroxyhexadecyl) oxyhexandecanoic acid.

* * * * *

UNITED STATES PATENT AND TRADEMARK OFFICE
CERTIFICATE OF CORRECTION

PATENT NO. : 6,852,686 B2 Page 1 of 1
APPLICATION NO. : 10/023275
DATED : February 8, 2005
INVENTOR(S) : Steinert et al.

It is certified that error appears in the above-identified patent and that said Letters Patent is hereby corrected as shown below:

Column 44, line 59, in claim 3, delete "phosphatidyicholine" and insert --phosphatidylcholine--, therefor.

Column 44, line 61, in claim 4, delete "is" and insert --comprises--, therefor.

Column 44, line 61, in claim 4, delete "(16-hydroxyhexadecyl)" and insert --(16-hydroxyhexacecyl)--, therefor.

Signed and Sealed this

Twenty-first Day of November, 2006

JON W. DUDAS
*Director of the United States Patent and Trademark Office*